United States Patent [19]

Klioze et al.

[11] 4,424,357

[45] Jan. 3, 1984

[54] PROCESS FOR PREPARING 4-ARYLOXY-3-PHENYLPIPERIDINES

[75] Inventors: Solomon S. Klioze, Flemington; Frederick J. Ehrgott, Bernardsville, both of N.J.

[73] Assignee: Hoechst-Roussel Pharmaceuticals, Inc., Somerville, N.J.

[21] Appl. No.: 108,014

[22] Filed: Dec. 28, 1979

Related U.S. Application Data

[62] Division of Ser. No. 14,548, Feb. 23, 1979, Pat. No. 4,216,218.

[51] Int. Cl.$^3$ ............... C07D 211/46; C07D 405/06
[52] U.S. Cl. ............................. 546/207; 546/216; 546/221
[58] Field of Search ................. 546/207, 216, 221

[56] References Cited

PUBLICATIONS

Bittner, S., et al., *Chemistry and Industry*, 1975 (6), 281. TP1563
Grob, C., et al., *Tett. Lett.*, No. 30, 2613–2616 (1975).
Grob, C., *Angew. Chem. Int. Ed.*, 8(8), 535–622 (1969).
Grob, C., et al., *Angew, Chem. Int. Ed.*, 6(1), 1–106 (1967).
Gould, E., *Mechanism and Structure in Organic Chemistry*, Henry Holt and Co., New York, 1959, p. 278.

*Primary Examiner*—Richard A. Schwartz
*Attorney, Agent, or Firm*—Curtis, Morris & Safford

[57] ABSTRACT

Novel 4-aryloxy- and 4-arylthio-3-phenylpiperidines and related compounds, physiologically acceptable salts thereof and intermediates therefor possessing analgesic, antidepressant properties, and a process for the preparation of such compounds, derivatives and intermediates are described.

2 Claims, No Drawings

PROCESS FOR PREPARING 4-ARYLOXY-3-PHENYLPIPERIDINES

This is a division of application Ser. No. 14,548, filed Feb. 23, 1979, now U.S. Pat. No. 4,216,218.

This invention relates to 4-aryloxy- and 4-arylthio-3-phenylpiperidines, the physiologically acceptable salts thereof, and intermediates therefor, which are useful because of their pharmacological effect as analgesics and their action on the control of the central nervous system as antidepressants.

U.S. Pat. No. 3,542,794 describes 1-carbamoylbenzoylalkyl-, phenoxyalkyl- and ethoxycarbonyl-4-phenoxypiperidines as having muscle relaxant, anticonvulsant and tranquilizing properties. Other 4-phenoxypiperidines are described by R. F. Boswell et al., "Journal of Medicinal Chemistry," Vol. 17, No. 9, 1000 (1974). Neither teaches, suggests or discloses the compounds of the present invention or that such compounds may have pharmaceutical utility.

The compounds of the present invention have the formula

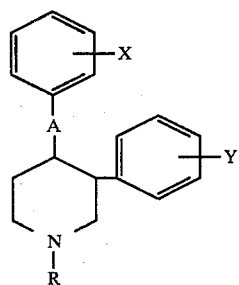

(I)

in which A is oxygen or sulfur; R is hydrogen, loweralkyl, cycloalkylloweralkyl, loweralkenyl, loweralkynyl, loweralkanoyl, cycloalkylloweralkanoyl, —COOR$_1$, or —R$_2$PhZ; R$_1$ is loweralkyl, loweralkenyl or —CH$_2$CCl$_3$; R$_2$ is loweralkylene [(CH$_2$)$_n$—], oxyloweralkylene [—(CH$_2$)$_n$—O—], loweralkylenecarbonyl [—(CH$_2$)$_n$CO—], carbonylloweralkylene [—CO(CH$_2$)$_n$—] or alkylene ethylene ketal

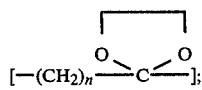

Ph is phenyl or phenylene; Z is hydrogen, halogen, loweralkyl, loweralkoxy, hydroxy, nitro or amino; n is 1, 2 or 3; and X and Y are the same or different and each can be hydrogen, loweralkyl, loweralkoxy, halogen, hydroxy, nitro, amino, acetamido, trifluoromethyl or cyano. In the above definitions, loweralkyl, loweralkenyl, loweralkynyl, loweralkoxy and loweralkanoyl mean those radicals of up to 6 carbon atoms. Cycloalkyl in the above definitions means those radicals of 3 to 6 carbon atoms.

Some of the compounds within the scope of this invention have greater pharmaceutical activity than others. Some of the latter such as those in which R is —COOR$_1$ or in which R$_2$ is loweralkylenecarbonyl are nevertheless desirable as intermediates for the preparation of the more active compounds.

Other intermediate compounds, which are also the subject of this invention and are useful in the preparation of the 4-aryloxy-3-phenylpiperidines, are depicted by the formula

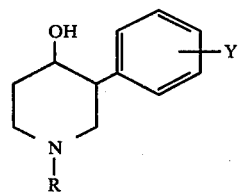

in which R and Y are as previously defined.

The compounds of the present invention encompass both the cis structural isomer as shown in Formula I(a) below:

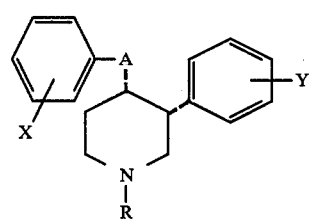

I(a)

and the trans structural isomer as shown in Formula I(b) below.

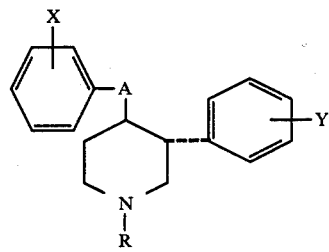

(Ib)

Identification of these isomers is readily made using techniques well known to those skilled in the art and described, for example, in Jackman and Sternnell, "Applications of NMR Spectroscopy," Pergamon Press, 1969.

As to the physiologically acceptable salts, those coming within the purview of this invention include pharmaceutically acceptable acid-addition salts. Acids useful for preparing these acid-addition salts include inter alia, inorganic acids, such as the hydrohalic acids, e.g., hydrochloric and hydrobromic acids, sulfuric acid, nitric acid and perchloric acid, and organic acids such as oxalic, malonic, succinic, maleic, fumaric, tartaric, citric, acetic, benzoic, salicylic, etc.

The compounds of the present invention can be prepared according to the following sequence of reactions in which R, X, Z, Ph and Y are as previously defined, unless otherwise indicated.

METHOD A

1. An ethyl β-substituted aminopropionate of the formula

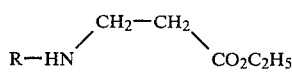

is prepared by any conventional technique. Typically, an alcoholic solution of a substituted amine, e.g., methylamine is reacted with ethyl acrylate at 0° C. to 25° C. for 30 to 90 hours.

2. A diethyl-2-oxo-3-phenylsuccinate sodium salt of the formula

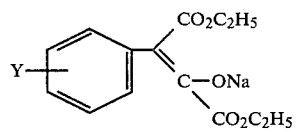

is prepared by adding ethanol to a suspension of sodium hydride in xylene while maintaining the resulting mixture below 30° C. to form a solution of sodium ethoxide. Diethyl oxalate is then added to the solution followed by addition thereto of an aromatic substituted acetate ester, e.g., an ethyl phenylacetate. The resultant reaction mixture is maintained at a temperature of 10° to 25° C. for 6 to 20 hours under a nitrogen atmosphere.

3. A compound of Formula III is combined and reacted with formaldehyde in an aqueous medium at a temperature below 25° C. for a period of time typically ranging from 15 to 60 minutes. Potassium carbonate is then added in portions to the resultant reaction mixture, while the temperature thereof is maintained below 25° C. The reaction mixture is then vigorously stirred, e.g., 0.5 to 3 hours, under a nitrogen atmosphere to form an ethyl atropate of the formula.

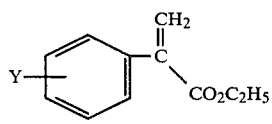

4. The compound of Formula II is combined with the compound of Formula IV and stirred at ambient temperature for a period of time, e.g., 15 to 24 hours, to form via a Michael condensation, an ethyl N-(2-ethoxycarbonylethyl)-3-amino-2-phenylpropionate of the formula

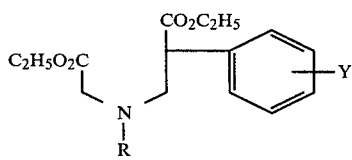

5. The compound of Formula V is added along with a catalytic amount of ethanol to a suspension of sodium hydride in toluene and heated to reflux, e.g., typically for 10 to 60 minutes. The reaction mixture is cooled to room temperature, and a mineral acid, e.g., 6 N-hydrochloric acid, is added thereto followed by refluxing the acidified portion thereof, typically for 1 to 3 hours to form a key intermediate of a 3-phenyl-4-piperidone of the formula

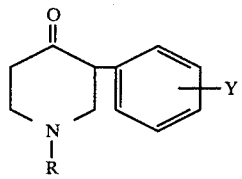

The above sequence of reactions is a variant of the procedure of A. A. Patchett, F. G. Giarrusso, "Journal of Medicinal and Pharmaceutical Chemistry", Vol. 4, 385 (1961).

6. The compound of Formula VI is reduced using any conventional technique to a 3-phenyl-4-piperidinol of the formula

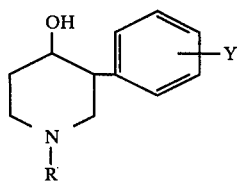

The compound of Formula VII may be either cis or trans.

In one method of proceeding, the compound of Formula VI is reduced by adding to an absolute ethanol solution thereof a reducing agent comprising sodium borohydride. The reaction mixture is typically maintained at 0° to 25° C. for one to 18 hours to form a mixture of the cis- and trans isomers having the formulae:

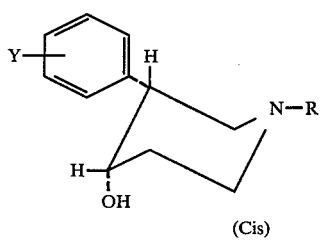

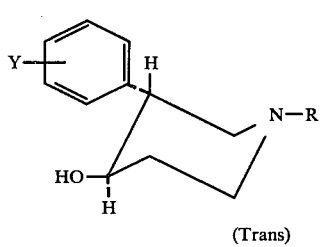

These isomers can be separated using conventional techniques known in the art, such as, for example, column chromatography and fractional crystallization.

In another manner of proceeding, the compound of Formula VI is reduced by adding to a tetrahydrofuran solution thereof a reducing agent comprising lithium tri-secondarybutylborohydride. The reaction mixture is typically maintained at 0° to 25° C. for 3 to 18 hours. A basic solution, e.g., aq. NaOH, and aqueous hydrogen peroxide solution is then added to the resultant reaction mixture, which is maintained between 30° and 40° C., followed by stirring at room temperature with subsequent refluxing for one to 3 hours to form only the cis isomer as depicted in Formula VIIa above.

7. The compound of Formula VII (cis, trans, or a mixture thereof) is combined with sodium hydride in an appropriate solvent, e.g., dimethylformamide, and heated to 60° to 90° C. under a nitrogen atmosphere until hydrogen evolution ceases, e.g., typically, 1 to 1.5 hours. The reaction mixture is cooled to room temperature and either a substituted or unsubstituted fluorobenzene is added thereto. The resultant reaction mixture is then maintained at room temperature with stirring under a nitrogen atmosphere for a period of time, e.g., 18 to 72 hours, to form a 4-aryloxy-3-phenylpiperidine of the invention depicted by the formula

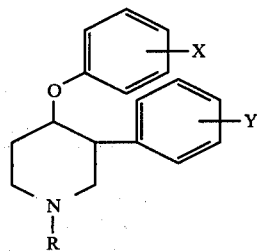

(VIII)

which can be either the cis isomer or the trans isomer.

When X or Y or both are nitro, it is understood that any conventional reduction thereof can be carried out to form the amino group.

When R is not hydrogen, the resultant product of Formula VIII may have the R group removed, e.g., by dealkylation, using any standard means, such as for example, by reaction with ethyl chloroformate, vinyl chloroformate or 2,2,2-trichloroethyl chloroformate, followed by hydrolysis of the resultant reaction product to form a compound of Formula VIII in which R is hydrogen.

When X or Y or both are loweralkoxy, they may be converted to hydroxy via conventional means such as by treatment with boron tribromide or pyridine hydrochloride.

METHOD B

The compound of Formula VIIa is combined with either a substituted phenol, e.g., a cresol, or an unsubstituted phenol, triphenylphosphine, and a solvent, e.g., benzene. Diethyl azodicarboxylate is then added to the resultant solution. The resultant reaction mixture is then maintained under a nitrogen atmosphere at room temperature, typically for 6 to 30 hours, to form the product of Formula VIII in the trans isomer form. Alternatively, the compound of Formula VIIb wherein R is —COOR₁ or COR can be so reacted to form the product of Formula VIII in the cis isomer form wherein R is so limited.

METHOD C

Compounds of the invention of the formula

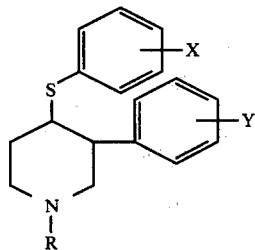

(IX)

(cis or trans) are prepared as follows. An N-phenylthiophthalimide of the formula

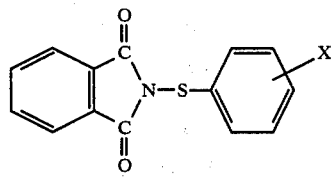

(X)

wherein X is neither hydroxy nor amino, is combined with tri-n-butylphosphine under nitrogen, typically at room temperature for 15 minutes. To the resultant mixture is added the compound of Formula VII (cis or trans), which is then typically maintained at room temperature for 24 hours to yield an arylthiophenylpiperidine compound of the invention.

When X or Y or both are nitro, it is understood that any conventional reduction thereof can be carried out to form the amino group.

When R is not hydrogen, the resultant product of Formula IX may have the R group removed, e.g. by dealkylation, using any standard means, such as for example, by reaction with ethyl chloroformate, vinyl chloroformate or 2,2,2-trichloroethyl chloroformate, followed by hydrolysis of the resultant reaction product to form a compound of Formula IX in which R is hydrogen.

When X or Y or both are loweralkoxy, it is understood that they may be converted to hydrogen via conventional means such as by treatment with boron tribromide or pyridine hydrochloride.

METHOD D

A compound of the invention of the formula

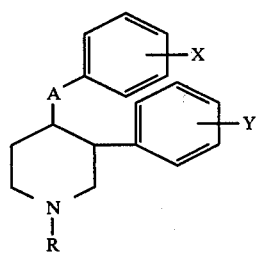

(XI)

in which R is loweralkanoyl, cycloalkylloweracyl or —CO(CH₂)ₙPhZ is prepared as follows: The compound of Formula VIII, where R is hydrogen, or the compound of Formula IX, where R is hydrogen, is reacted, e.g., 2 hours at room temperature, with an acyl halide selected from a loweralkanoyl halide, a cycloalkylloweralkanoyl halide or a phenylalkanoyl halide, e.g., Ph(CH$_2$)$_n$COCl to yield the desired compound.

METHOD E

The compounds of Formulae VIII and IX, when R is alkoxycarbonyl, alkenyloxycarbonyl, trichloroethoxycarbonyl or —R$_2$PhZ or the compound of Formula XI can be reduced to yield a compound wherein R is loweralkyl, cycloalkylloweralkyl or phenalkyl. Any suitable conventional reducing agent may be employed. For example, a selected compound, such as a compound of Formula XI is typically reacted with borane to achieve the desired reduction.

METHOD F

The compounds of Formulae VIII and IX, when R is hydrogen, can be alkylated to form the corresponding compounds in which R is loweralkyl, loweralkynyl, loweralkenyl, cycloalkylloweralkyl, phenylloweralkyl or

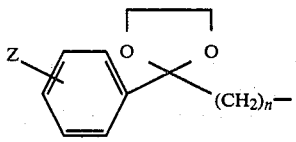

The selected compound (VIII or IX, when R is hydrogen) is reacted with a halide, depicted by R-Z$^1$, where R is loweralkyl, loweralkynyl, loweralkenyl, cycloalkylloweralkyl, phenylloweralkyl or

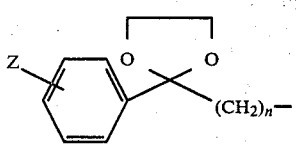

and Z$^1$ is halogen, in the presence of an inorganic halide, e.g., KI, under basic conditions. Typically, the reaction is carried out at an elevated temperature, e.g. 90° C., for an extended period of time, e.g. 18 hours, whereby the desired alkylated compound is obtained.

When R is

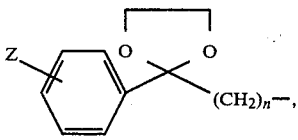

the compound can be treated with an acid, e.g. hydrochloric acid, to form a compound in which R is —(CH$_2$)$_n$COPhZ.

METHOD G

The compounds of Formulae VIII and IX can, when X or Y or both are amino, be converted to corresponding compounds in which X or Y or both are acetamido. Any suitable acetyl halide can be employed, for example, a selected compound (VIII, IX) is typically reacted with acetyl chloride to form the corresponding acetamido compound.

In each of the above reaction steps, optimum conditions depend upon starting materials, solvents, catalysts and other reaction components as will become more apparent in the examples given below.

The utility of the compounds of the present invention in the treatment of depression in mammals is demonstrated by their ability to inhibit tetrabenazine induced depression in mice [International Journal of Neuropharmacology 8, 73 (1969)], a standard assay for useful antidepressant properties. Thus, for instance, on oral dose of 1.5 mg/kg of body weight of cis-1-methyl-4-(4-nitrophenoxy)-3-phenylpiperidine maleate inhibits tetrabenazine induced depression in mice.

The same inhibition by dosage of other compounds occurs as follows:

| Compound | Dose (mg/kg) |
|---|---|
| trans-4-(4-aminophenoxy)-1-methyl-3-phenylpiperidine | 1.7 (oral) |
| trans-1-methyl-4-phenoxy-3-phenylpiperidine oxalate | 3.2 (intraperitoneal) |
| cis-4-(4-aminophenoxy)-1-methyl-3-phenylpiperidine dihydrochloride | 4.9 (oral) |
| trans-4-(4-cyanophenoxy)-1-methyl-3-phenylpiperidine oxalate | 7.7 (intraperitoneal) |
| cis-1-methyl-3-phenyl-3-piperidinol | 20 (intraperitoneal) |

These data indicate that the compounds of the present invention would be useful as antidepressants in mammals when administered in amounts ranging from 0.1 to 100 mg/kg of body weight per day.

Compounds of the invention are useful as analgesic agents due to their ability to alleviate pain in mammals. The activity of the compound is demonstrated in the 2-phenyl-1, 4-benzoquinone-induced writhing test in mice, a standard asay for analgesia [Proc. Soc. Exptl. Biol. Med. 95, 729 (1975)]. For example, at subcutaneous doses of 0.37, 0.56, 1.9, 2.1, 3.6, 7.6, 9.9 and 13.4 mg/kg of body weight of trans-4-(4-fluorophenoxy)-1-methyl-3-phenylpiperidine; trans-1-methyl-3-phenyl-4-(4-tolyl) piperidine maleate; trans-4-(4-aminophenoxy)-1-methyl-3-phenylpiperidine, trans-1-methyl-4-phenoxy-3-phenylpiperidine oxalate; cis-4-(4-aminophenoxy)-1-methyl-3-phenylpiperidine dihydrochloride; cis-1-methyl-4-(4-nitrophenoxy)-3-phenylpiperidine maleate; trans-4-(4-cyanophenoxy)-1-methyl-3-phenylpiperidine oxalate; and cis-1-methyl-3-phenyl-4-piperidinol, respectively, exhibit an approximately 50% inhibition of writhing.

The above data illustrate that the compounds of the present invention are useful as analgesics when administered to mammals at doses of from 0.1 to 100 mg/kg of body weight per day.

Examples of the compounds of the invention are:
trans-4-(4-hydroxyphenoxy)-1-methyl-3-phenylpiperidine;
cis-4-(4-chlorophenoxy)-3-(3-chlorophenoxy)-1-(4-chlorophenethyl)piperidine;
cis-1-(4-aminophenethyl)-4-(4-chlorophenoxy)-3-(2-tolyl)piperidine;
trans-1-allyl-4-(4-fluorophenoxy)-3-(3-methoxyphenyl)piperidine;
trans-1-cyclopropylmethyl-4-(4-fluorophenoxy)-3-phenylpiperidine;
trans-4-(4-fluorophenoxy)-3-(2-fluorophenyl)-1-propargylpiperidine;
cis-1-(3-nitrophenethyl)-3-phenyl-4-(4-tolyloxy)piperidine;

cis-1-[3-(3-chlorophenyl)propyl]-3-phenyl-4-(3-tolyloxy)piperidine;
trans-4-(4-fluorophenoxy)-3-(3-hydroxyphenyl)-1-(3-methyl-2-butenyl)piperidine;
cis-1-(3-methoxyphenethyl)-3-phenyl-4-(2-tolyloxy)-piperidine;
trans-1-benzoylethyl-4-(4-fluorophenoxy)-3-phenylpiperidine;
cis-4-(2-chlorophenoxy)-3-phenyl-1-(3-tolylethyl)-piperidine;
trans-4-(3-fluorophenoxy)-1-(4-hydroxyphenethyl)-3-phenylpiperidine;
cis-4-(2-chlorophenoxy)-3-(3-chlorophenyl)-1-(4-methoxyphenyl propionyl)piperidine.
cis-4-(4-hydroxyphenoxy)-1-methyl-3-phenylpiperidine;
cis-1-methyl-3-(3-nitrophenyl)-4-phenoxypiperidine;
trans-3-(3-aminophenyl)-1-methyl-4-phenoxypiperidine;
cis-3-(3-acetamidophenyl)-1-methyl-4-phenoxypiperidine;
trans-3-(3-trifluoromethylphenyl)-1-methyl-4-phenoxypiperidine;
cis-3-(3-cyanophenyl)-1-methyl-4-phenoxypiperidine;
trans-4-(4-chlorophenoxy)-3-phenyl-1-(2,2,2-trichloroethylcarbonyl)piperidine;
trans-4-(4-fluorophenoxy)-1-(3-phenoxypropyl)-3-phenylpiperidine;
cis-1-[3-(4-chlorophenoxy)propyl]-4-phenoxy-3-phenylpiperidine;
trans-1-(butylcarbonyl)-3-phenyl-4-(2-tolyloxy)piperidine;
cis-1-(2-cyclopropylpentylcarbonyl)-3-phenyl-4-(2-tolyloxy)piperidine;
trans-1-(3-methoxybenzoyl)ethyl-4-phenoxy-3-phenylpiperidin
cis-1-(3-chlorophenylacetyl)-4-(4-nitrophenoxy)-3-phenylpiperidine;
trans-4-(3-fluorophenoxy)-1-[3-(3-methoxyphenoxy)propyl]-3-phenylpiperidine;
trans-4-(3-fluorophenoxy)-1-[3-(3-hydroxyphenoxy)propyl]-3-phenylpiperidine;
cis-4-(2-chlorophenoxy)-3-(3-chlorophenyl)-1-(4-hydroxyphenylpropionyl)piperidine;
trans-1-(3-hydroxybenzoyl)ethyl-4-phenoxy-3-phenylpiperidine;
cis-1-[3-(4-nitrophenoxy)propyl]-3-phenyl-4-(2-tolyloxy)piperidine;
trans-1-(4-nitrophenylacetyl)-4-phenoxy-3-phenylpiperidine;
cis-4-(4-cyanophenoxy)-1-(2-nitrobenzoyl)ethyl-3-phenylpiperidine;
cis-1-[3-(4-aminophenoxy)propyl]-3-phenyl-4-(2-tolyloxy)piperidine;
trans-1-(4-aminophenylacetyl)-4-phenoxy-3-phenylpiperidine;
cis-1-(2-aminobenzoyl)ethyl-4-(4-cyanophenoxy)-3-phenylpiperidine;
trans-4-(4-fluorophenoxy)-3-phenyl-1-[3-(2-tolyloxy)propyl]piperidine;
trans-4-(4-fluorophenoxy)-3-(2-fluorophenyl)-1-(2-tolylacetyl)piperidine; and
cis-1-(2-methylbenzoyl)ethyl-3-phenyl-4-(4-trifluoromethylphenoxy)piperidine.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently contain between 4% to about 70% of the weight of the unit. The amount of active compound in such compositions and preparations according to the present invention are such that an oral dosage unit form contains between 1.0–3000 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; a sweetening agent such as sucrose or saccarin; or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a suspension. These preparations should contain at least 0.1% active compound, but may be varied to be between 0.5 and about 50% of the weight therof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE 1 a. Ethyl β-methylaminopropionate

Gaseous methylamine is bubbled into 2.5 l. of absolute alcohol, maintained at 0° C., for 80 minutes. To this solution is added dropwise, with stirring under a nitrogen atmosphere, a solution of 200.24 g. of ethyl acrylate in 500 ml of absolute alcohol. The resultant solution is stirred at room temperature for 46 hours. The solvent is removed in vacuo to afford a nearly colorless liquid. Vacuum distillation gives a colorless liquid product of ethyl-β-methylaminopropionate having a boiling point of 74°–76° C. at 23 mm of Hg (82°–85° C. at 32 mm Hg).

b. Diethyl 2-oxo-3-phenylsuccinate sodium salt 170 ml of absolute ethanol is added to a suspension of 67.2 g of sodium hydride in 1.34 of xylene. The temperature of the resultant mixture is maintained below 30° C. and 339 ml of diethyl oxalate are added thereto. When hydrogen evolution slows, 397 ml of ethylphenylacetate are added. A solid precipitates and the resultant mixture is stirred for 18 hours under a nitrogen atmosphere. The solid product is filtered, washed with ether and then dried for 18 hours in vacuo at 60° C. over KOH. Diethyl 2-oxo-3-phenylsuccinate sodium salt is obtained as a solid product.

c. Ethyl atropate 225 ml of 37 weight percent aqueous formaldehyde solution are added dropwise with stirring to a solution of 316 g of diethyl 2-oxo-3-phenylsuccinate sodium salt and 560 ml of water. During the addition, the mixture is maintained at a temperature below 25° C. The mixture is stirred for one hour at room temperature and then 152 g of anhydrous $K_2CO_3$ are added in portions over a ten minute period, while the temperature is maintained below 25° C. The resultant mixture is vigorously stirred for 1.5 hours at room temperature under a nitrogen atmosphere. The reaction mixture is diluted with 1500 ml of water and extracted with one 2.5 l. portion of ether followed by two 1.25 l portions of ether. The ether is removed and a product comprising an oil of ethyl atropate is obtained.

d. Ethyl N-(2-ethoxycarbonylethyl)-3-methylamino-2-phenylpropionate 184.47 g of ethyl atropate (of Example 1c) are added dropwise, over a 20 minute period, to 132.16 g of ethyl β-methylaminopropionate (of Example 1a). The mixture is stirred for 18 hours at room temperature under a nitrogen atmosphere. The mixture is combined with 1.8 l. of ether and then the resultant mixture is extracted with two 800 ml portions of 2 N hydrochloric acid. The acid solution is extracted with two 150 ml portions of ether. The aqueous extracts are basified with 50 weight percent aqueous NaOH solution and then extracted with three 900 ml portions of ether. The ether extracts are combined and dried for 18 hours over $MgSO_4$. The combined ether portions are filtered and concentrated in vacuo to yield ethyl N-(2-ethoxycarbonylethyl)-3-methylamino-2-phenylpropionate.

e. 1-Methyl-3-phenyl-4-piperidone 208.78 g of ethyl N-(2-ethoxycarbonylethyl)-3-methylamino-2-phenylpropionate, 10 ml of absolute alcohol and 500 ml of toluene are added to a suspension of 65.28 g of sodium hydride and 3.0 l of toluene. When hydrogen evolution slows (about 0.5 hour), the mixture is heated to reflux for 30 minutes. The reaction mixture is cooled and then extracted with 6 N hydrochloric acid. The resultant acid extracts are washed with 500 ml of hexane and heated to reflux under nitrogen for two hours. The mixture is then cooled, basified with 50 weight percent aqueous NaOH solution (1.6 l) and then extracted with ether. The ether extracts are dried over $Na_2SO_4$ and then filtered. The filtrate is concentrated in vacuo to yield an oil product of 1-methyl-3-phenyl-4-piperidone.

f. Trans-1-methyl-3-phenyl-4-piperidinol oxalate 2.66 g of sodium borohydride are added, in several portions, to a solution of 13.25 g of 1-methyl-3-phenyl-4-piperidone in 200 ml of absolute ethanol. After stirring at ambient temperature for 3 hours, the mixture is diluted with 800 ml of water and extracted with chloroform. The chloroform extracts are dried over anhydrous $MgSO_4$, filtered, and concentrated in vacuo to a semi-solid which TLC shows to be a mixture of isomers. The resultant material is triturated with an ether:hexane mixture and the solid is filtered off. TLC shows the crude solid to be mostly the minor reduction product (cis) while the filtrate contains predominantly the other isomer (trans). The filtrate is chromatographed on 240 g of silica gel. The product is eluted with 25% methanol/acetone mixture. An oil which TLC shows to contain only the major product of trans isomer (free base) is taken up in 15 ml of absolute ethanol and the latter is added to a warm solution of 0.98 g of oxalic acid in 15 ml of ethanol. The volume of solvent is reduced to approximately 20 ml by boiling off some of the ethanol, and then the solution is allowed to cool and stand for a few hours. The material which crystallized out is filtered, washed with cold ethanol, then ether, and dried to yield crystals, m.p. 158.5°–161° C. dec., of trans-1-methyl-3-phenyl-4-piperidinol oxalate. This trans isomer is assigned the equatorial OH, or trans configuration based on the chemical shift of the proton α to the OH in isomeric cyclohexanols (Jackman and Sternnell, "Applicants of NMR Spectroscopy", p 239, Pergamon Press, 1969).

Analysis: Calculated for $C_{14}H_{19}NO_5$: 59.78%C; 6.81%H; 4.98%N. Found: 59.53%C; 6.83%H; 4.84%N.

g. Cis-1-methyl-3-phenyl-4-piperidinol

The crude solid of Example 1f, above, is recrystallized from benzene to yield a crystalline solid, m.p. s 127°, 130.5°–132.5° C., which NMR and TLC showed to be essentially one isomer, namely, cis-1-methyl-3-phenyl-4-piperidinol. This isomer is assigned the axial OH, or cis, configuration based on the chemical shift of the proton α to the OH group in isomeric cyclohexanols (Jackman and Sternnell, "Applications of NMR Spectroscopy," p. 239, Pergamon Press, 1969.

Analysis: Calculated for $C_{12}H_{17}NO$: 75.35%C. 8.96%H. 7.32%N. Found: 75.24%C. 8.96%H. 7.39%N.

h. Trans-1-methyl-3-phenyl-4-(4-trifluoromethylphenoxy)piperidine oxalate

A mixture of 3.0 g of trans 1-methyl-3-phenyl-4-piperidinol (free base), 0.46 g of sodium hydride, 2.63 g of 4-trifluoromethylfluorobenzene and 30 ml of dimethylformamide (DMF) is heated to 90° C., at which point vigorous hydrogen evolution occurs. When gas evolution slows, the mixture is allowed to cool to room temperature. Another 2.63 g of the aryl fluoride is added, and the mixture is allowed to stir 18 hours at room temperature under a nitrogen atmosphere. The reaction mixture is poured into 100 ml of water and extracted with dichloromethane. The organic extracts are washed with water and saturated aqueous NaCl solution, dried over anhydrous $Na_2SO_4$, and concentrated in vacuo to an oil containing some DMF. The oil is partitioned between 100 ml of saturated aqueous NaCl solution and 100 ml of ether. The ether phase is washed with two 100 ml portions of water, dried over anhydrous $MgSO_4$, and concentrated in vacuo to an oil which crystallizes upon standing. This material is chromatographed on 160 g of silica gel. The product is eluted, using 25% methanol-/acetone as solvent. This material (m.p. s 65.5°–68° C.) is dissolved in 25 ml of absolute ethanol and treated with a warm solution of 0.59 g of oxalic acid in 25 ml of absolute ethanol. The volume of solvent is boiled down to 20 ml, and the solution is allowed to cool to room temperature. Scratching causes crystallization to occur. The solid is filtered, washed with cold ethanol and then ether to afford a solid, m.p. s 116°, 164.5°–166° C. dec. of trans-1-methyl-3-phenyl-4-(4-trifluoromethylphenoxy)piperidine oxalate.

Analysis: Calculated for $C_{19}H_{20}F_3NO.(CO_2H)_2$: 59.29%C; 5.21%H; 3.29%N; 13.40%F. Found: 59.38%C; 5.09%H; 3.28%N; 13.23%F.

EXAMPLE 2

Trans-4-(4-cyanophenoxy)-1-methyl-3-phenylpiperidine oxalate

A mixture of 3.99 g 1-methyl-3-phenyl-4-piperidinol (the mixture of isomers of Example 1), 0.55 g sodium hydride, and 20 ml of DMF is heated to 70°–80° C. under nitrogen until hydrogen evolution ceases. The mixture is cooled to room temperature and a solution of 2.79 g of p-fluorobenzonitrile in 10 ml of DMF is added. After stirring 16 hours at room temperature the mixture is poured into water and extracted with dichloromethane. The latter is washed with water and saturated aqueous NaCl solution and dried over anhydrous $Na_2SO_4$. The solvent is removed in vacuo and the resulting oil is partitioned between ether and saturated aqueous NaCl solution. The ether phase is washed with water and dried over anhydrous $MgSO_4$. Removal of the solvent in vacuo affords an oil which is chromatographed on silica gel, using acetone and then 25% methanol/acetone as solvent. A crude product is obtained as an oil which crystallizes upon standing (m.p. s 83.5°, 84.5°–87° C.). This material is taken up in 25 ml of absolute ethanol and treated with a warm solution of 0.64 g of oxalic acid in 25 ml of absolute ethanol. The volume of solvent is boiled down to 40 ml and the precipitated solid is filtered, washed with ethanol, then ether to afford a crystalline solid, m.p. s 93.5°, 111°–114° C., of trans-4-(4-cyanophenoxy)-1-methyl-3-phenylpiperidine oxalate.

Analysis: Calculated for $C_{19}H_{20}N_2O.(CO_2H)_2$: 65.96%C; 5.80%H; 7.33%N. Found: 66.20%C; 6.02%H; 7.21%N.

EXAMPLE 3

Trans-1-methyl-4-(4-nitrophenoxy)-3-phenylpiperidine maleate

A mixture of 0.91 g of sodium hydride, 7.24 g of 1-methyl-3-phenyl-4-piperidinol (mixture of isomers of Example 1) and 60 ml of anhydrous DMF is heated to 95° C. under nitrogen. When hydrogen evolution ceases (approximately 1 hr.) the mixture is cooled in an ice-water bath and treated with a solution of 5.9 g of 4-nitrofluorobenzene in 30 ml of DMF (added dropwise over a 10-minute period). After stirring 18 hours at room temperature under a nitrogen atmosphere the mixture is poured into water and extracted with chloroform. The chloroform extracts are dried over anhydrous $Na_2SO_4$, filtered and concentrated in vacuo to an oil containing DMF. The oil is partitioned between ether and saturated aqueous NaCl solution. The aqueous phase is extracted with ether. The combined ether extracts are washed with water, dried, and concentrated in vacuo to a semisolid. This semisolid material is chromatographed on silica gel, using 25% methanol/acetone solution as solvent. The crude trans isomer is obtained as a solid, m.p. s 94.5°, 96.5°–99° C. A portion of this material (the free base) is taken up in 20 ml of warm absolute ethanol and treated with a solution of 0.74 g of maleic acid in a mixture of 30 ml ether and 3 ml of absolute ethanol. The solvent is removed in vacuo and the resulting oil is triturated with ether containing a few ml of ethanol until crystallization occurs. The crude salt is recrystallized from ethyl acetate to afford crystals, m.p. s 152.5°, 154.5°–156.5° C., of trans-1-methyl-4-(4-nitrophenoxy)-3-phenylpiperidine maleate.

Analysis: Calculated for $C_{18}H_{20}N_2O_3.C_4H_4O_4$: 61.68%C; 5.65%H; 6.54%N. Found: 61.49%C; 5.64%H; 6.46%N.

EXAMPLE 4 a.

Trans-1-ethoxycarbonyl-4-(4-nitrophenoxy)-3-phenylpiperidine

A mixture of 3.63 g of the free base of Example 3, 1.6 g of anhydrous potassium carbonate and 25 ml of anhydrous benzene is treated with 1.22 ml of ethyl chloroformate, and the mixture is allowed to reflux 18 hours under nitrogen. Then another 0.44 ml of ethyl chloroformate is added and the mixture is refluxed 18 hours, then poured into a mixture of 100 ml of water and 100 ml of ether. The aqueous phase is extracted with ether. The combined ether extracts are washed with water and saturated aqueous NaCl solution, dried over $Na_2SO_4$, filtered and concentrated in vacuo to a gum. This material is chromatographed on silica gel, using chloroform as solvent. A fraction of pure material and two fractions of slightly less pure material are obtained. The product of trans-1-ethoxycarbonyl-4-(4-nitrophenoxy)-3-phenylpiperidine is obtained as a glass.

Analysis: Calculated for $C_{20}H_{22}N_2O_5$: 64.85%C; 5.99%H; 7.56%N. Found: 64.99%C; 6.11%H; 7.45%N.

b. Trans-4-(4-nitrophenoxy)-3-phenylpiperidine maleate

A mixture of 2.88 g of trans 1-ethoxycarbonyl-4-(4-nitrophenoxy)-3-phenylpiperidine, 40 ml of absolute ethanol and 19 ml of 20% aqueous NaOH solution is refluxed 18 hours under nitrogen. The ethanol is then removed in vacuo and the aqueous residue partitioned between ether and water. The aqueous phase is extracted with ether, and then the combined ether extracts are washed with water and saturated aqueous NaCl solution. After drying over anhydrous $Na_2SO_4$, removal of the solvent in vacuo affords a yellow gum. This material is dissolved in ether and a solution of 0.76 g of maleic acid in 100 ml of ether is added dropwise.

The resulting yellow solid is filtered, washed with ether, and dried in vacuo to afford a fused glass. Trituration of this material with 350 ml of boiling ethyl acetate causes the gum to crystallize into a nearly colorless solid. The mixture is cooled for several hours, then filtered, and the solid is washed with cold ethyl acetate, then ether, and dried to afford a solid product, m.p. s 165°, 166°–167° C., of trans-4-(4-nitrophenoxy)-3-phenylpiperidine maleate.

Analysis: Calculated for $C_{17}H_{18}N_2O_3 \cdot C_4H_4O_4$: 60.86%C; 5.35%H; 6.76%N. Found: 61.08%C; 5.36%H; 6.78%N.

EXAMPLE 5 a. Trans-4-(4-nitrophenoxy)-3-phenylpiperidine hydrochloride

The procedure of Example 4b is repeated except that instead of the maleate, a hydrochloride salt is prepared as follows: The yellow gum is dissolved in dichloromethane and a saturated solution of hydrogen chloride in ether is added dropwise. The resulting solid is then filtered, washed with ether and dried to afford a solid product, m.p. s 147°, 249.5°–251° C. dec., of trans-4-(4-nitrophenoxy)-3-phenylpiperidine hydrochloride.

b. Trans-4-(4-aminophenoxy)-3-phenylpiperidine hydrochloride

A solution of 3.06 g of trans-4-(4-nitrophenoxy)-3-phenyl piperidine hydrochloride in a mixture of 125 ml of absolute ethanol and 10 ml distilled water is hydrogenated over a 10% palladium on carbon catalyst for 18 hours at room temperature at 45 psi of hydrogen. The catalyst is filtered off, and the filtrate is concentrated in vacuo to afford a solid, m.p. sweats 140°, s 180°, 182.5°–185.5° C. Recrystallization from absolute ethanol affords a crystalline solid, m.p. s 190°, 191°–192° C., of trans-4-(4-aminophenoxy)-3-phenylpiperidine hydrochloride.

Analysis Calculated for $C_{17}H_{20}N_2O \cdot HCl$: 66.98%C; 6.95%H; 9.19%N; 11.63%Cl. Found: 67.0%C; 6.91%H; 9.17%N; 11.42%Cl.

EXAMPLE 6

Trans-4-(4-aminophenoxy)-1-methyl-3-phenylpiperidine

A solution of 3.12 g of the free base of Example 3 in 90 ml of absolute ethanol is hydrogenated over 0.31 g of 10% palladium on carbon catalyst at 45 psi and room temperature. Uptake stops within 2 hours. The catalyst is filtered off, and the filtrate is concentrated in vacuo to an oil which crystallizes upon standing 18 hours. This material is recrystallized from hexane to afford crystals, m.p. s 103°, 104.5°–106° C., of trans-4-(4-aminophenoxy)-1-methyl-3-phenylpiperidine.

Analysis: Calculated for $C_{18}H_{22}N_2O$: 76.55%C; 7.85%H; 9.92%N. Found: 76.62%C; 7.90%H; 9.95%N.

EXAMPLE 7

Cis-1-methyl-4-(4-nitrophenoxy)-3-phenylpiperidine maleate

The procedure of Example 3 is repeated, except as follows. After the material is chromatographed on silica gel, using 25% and then 50 volume percent methanol/acetone solution as solvent, the fractions containing the cis isomer are combined and concentrated in vacuo to a solid which is triturated with petroleum ether and filtered to afford a crude material, m.p. s 100°, 102°–105° C. (the free base). This material is dissolved in a mixture of 10 ml of absolute ethanol and 25 ml of ether and is treated with a solution of 0.77 g of maleic acid in 10 ml of ethanol. The solid which crystallizes is filtered, washed with ether and dried to afford a solid, m.p. s 172.5°, 173.5°–175.5° C., of cis-1-methyl-4-(4-nitrophenoxy)-3-phenylpiperidine maleate.

Analysis: Calculated for $C_{18}H_{20}N_2O_3 \cdot C_4H_4O_4$: 61.68%C; 5.65%H; 6.54%N. Found: 61.55%C; 5.62%H; 6.43%N.

EXAMPLE 8

Cis-4-(4-aminophenoxy)-1-methyl-3-phenylpiperidine dihydrochloride

A solution of 3.7 g of the free base of cis-1-methyl-4-(4-nitrophenoxy)-3-phenylpiperidine, of Example 7, in 100 ml of absolute ethanol is hydrogenated over 0.37 g of 10% Pd on carbon catalyst at 45 psi of hydrogen and room temperature. Uptake stops after 48 hours. The catalyst is filtered off and the filtrate is concentrated in vacuo to a gum. This material is chromatographed on silica gel using acetone and then 25% methanol/acetone as solvent. A purified free base is obtained and a portion of this material is dissolved in ether and is then added dropwise to a solution of dry HCl in ether. The resulting precipitate is filtered, washed with ether, and is then immediately suspended in boiling ether. Absolute ethanol is added until the mixture grows clear. Scratching of the cold solution causes crystallization to occur. The recrystallized solid is filtered, washed with cold acetone, then ether, and dried to afford a solid (m.p. 226°–227° C. dec.) of cis-4-(4-aminophenoxy)-1-methyl-3-phenylpiperidine dihydrochloride.

Analysis: Calculated for $C_{18}H_{22}N_2O \cdot 2HCl$: 60.84%C; 6.81%H; 7.89%N. Found: 60.92%C; 6.74%H; 7.72%N.

EXAMPLE 9

Cis-4-(4-nitrophenoxy)-3-phenyl-1-(2,2,2-trichloroethoxycarbonyl)piperidine 2.48 ml of 2,2,2-trichloroethyl chloroformate are added to a mixture of 4.69 g of the free base of Example 7, 2.07 g of anhydrous potassium carbonate and 45 ml of dry benzene. After stirring at room temperature for one hour, the mixture is refluxed 18 hours under nitrogen, then cooled and partitioned between a mixture of 200 ml of ether and 100 ml of water. The phases are separated and the aqueous phase is extracted with another 50 ml of ether. The combined organic extracts are washed with two 100 ml portions of water and 100 ml of saturated aqueous NaCl solution, dried over anhydrous MgSO$_4$ and concentrated in vacuo to a gum. This material is treated with approximately 150 ml of boiling hexane, and ether is added until the cloudy mixture grows clear. Refrigeration causes crystallization to occur. The yellow solid is filtered and washed with hexane to afford a crystalline material, m.p. s 103°, 105°–108° C., of cis-4-(4-nitrophenoxy)-3-phenyl-1-(2,2,2-trichloroethoxycarbonyl)piperidine.

Analysis: Calculated for $C_{20}H_{19}Cl_3N_2O_5$: 50.70%C; 4.04%H; 22.45%Cl; 5.91%N. Found: 50.97%C; 4.05%H; 22.15%Cl; 5.89%N.

EXAMPLE 10 a. Cis-4-(4-nitrophenoxy)-3-phenyl-1-vinyloxycarbonyl-piperidine

A solution of 4.58 g of vinyl chloroformate in 65 ml of 1,2-dichloroethane is cooled to −20° C. under nitrogen, and a solution of 10.19 g of the free base of Example 7 in 65 ml of dichloroethane is added dropwise at a rate which keeps the pot temperature near −20° C. (about 30 minutes). When the addition is complete, the bath and reaction mixture are allowed to slowly warm up. After 2 hours the pot temperature is 17° C. and the solvent is removed in vacuo. Trituration of the resulting gum with ether causes solidification to occur. The crude solid is filtered, washed with ether, and dried to afford a solid, mp s 118, 122°–125° C. of cis-4-(4-nitrophenoxy)-3-phenyl-1-vinyloxycarbonylpiperidine. Refrigeration of the ether filtrate yields additional product, mp s 121, 125.5°–128° C. Recrystallization from isopropanol yields product, mp s 123.5, 124°–127° C.

Analysis: Calculated for $C_{20}H_{20}N_2O_5$: 65.21%C; 5.47%H; 7.60%N. Found: 65.41%C; 5.52%H; 7.75%N.

b. Cis-4-(4-nitrophenoxy)-3-phenylpiperidine hydrochloride

A suspension of 6.44 g of cis-4-(4-nitrophenoxy)-3-phenyl-1-vinyloxycarbonylpiperidine in 250 ml of dry methaol is saturated with dry HCl gas and the resulting solution is stirred 18 hours at room temperature under a nitrogen atmosphere. The solvent is then removed in vacuo to afford a crude foam. Trituration of this material with 50 ml of boiling acetone for 20 minutes causes formation of a solid. The mixture is cooled and filtered, and the solid is washed with cold acetone and then ether to afford a product, m.p. s 220°, 222°–223.5° C. of cis-4-(4-nitrophenoxy)-3-phenylpiperidine hydrochloride.

Analysis: Calculated for $C_{17}H_{18}N_2O_3$.HCl: 60.98%C; 5.72%H; 8.37%N; 10.59%Cl. Found: 60.99%C; 5.75%H; 8.45%N; 10.54%Cl.

EXAMPLE 11

Cis-4-(4-aminophenoxy-3-phenylpiperidine hydrochloride

A solution of 4.1 g of cis-4-(4-nitrophenoxy)-3-phenylpiperidine hydrochloride, of Example 10, in a mixture of 125 ml of 95% aqueous ethanol and 5 ml of water is hydrogenated at 45 psi of hydrogen at room temperature over 0.41 g of 10% palladium on carbon catalyst. After 18 hours the catalyst is filtered off and the filtrate concentrated in vacuo. The resulting solid is triturated with ether and filtered to afford a nearly white salt, m.p. s 221°, 223.5°–225.5° C., of cis-4-(4-aminophenoxy)-3-phenylpiperidine hydrochloride.

Analysis: Calculated for $C_{17}H_{20}N_2O$.HCl: 66.98%C; 6.95%H; 9.19%N; 11.63%Cl. Found: 66.80%C; 7.01%H; 9.20%N; 11.72%Cl.

EXAMPLE 12

Cis-1-methyl-4-(2-nitrophenoxy)-3-phenylpiperidine hydrochloride

A suspension of 11.95 g of 1-methyl-3-phenyl-4-piperidinol (as a mixture of isomers of Example 1) in 150 ml of benzene, under nitrogen is added to a suspension of 1.87 of sodium hydride in 75 ml of dry benzene. The mixture is heated to reflux and 35 ml of dry DMF are added dropwise to the refluxing mixture over a 15-minute period. After 1 hour the mixture is cooled to room temperature, and a solution of 11.01 g of 2-nitrofluorobenzene in 75 ml of benzene is added all at once. A rise in temperature to 38° C. occurs. The mixture is stirred 18 hours at room temperature under nitrogen, then partitioned between saturated aqueous NaCl solution and ether. The phases are separated and the aqueous phase is extracted with ether. The combined organic extracts are washed with water, then with saturated aqueous NaCl solution, dried over anhydrous $Na_2SO_4$, and concentrated in vacuo to an oil. This material is taken up in 750 ml of dichloromethane and washed with 2 N HCl solution. The dichloromethane phase is washed with 5% aqueous $K_2CO_3$ solution, water, saturated aqueous NaCl solution, dried over anhydrous $Na_2SO_4$, and concentrated in vacuo to afford an oil. This oil is chromatographed on silica gel, using acetone, then 25% and finally 50% methanol/acetone solution as solvent. In this manner a purified cis isomer is obtained as the free base. The hydrochloride salt is prepared by dissolving the free base in dichloromethane and treating with an HCl-saturated ether solution. The solvent is removed in vacuo; trituration of the resulting gum with ether causes solidification to occur. The solid which results is filtered and washed with ether to afford a product, m.p. s 195°, 196.5°–199° C., of cis-1-methyl-4-(2-nitrophenoxy)-3-phenylpiperidine hydrochloride.

Analysis: Calculated for $C_{18}H_{20}N_2O_3$.HCl: 61.97%C; 6.07%H; 8.03%N; 10.17%Cl. Found: 61.87%C; 5.73%H; 7.97%N; 9.87%Cl.

EXAMPLE 13

Cis-4-(2-aminophenoxy)-1-methyl-3-phenylpiperidine hydrochloride

A solution of 4.26 g of cis-1-methyl-4-(2-nitrophenoxy)-3-phenylpiperidine hydrochloride of Example 12 in 125 ml of 95% aqueous ethanol (190 proof) is hydrogenated over 0.43 g of 10% palladium on carbon catalyst at 45 psi of hydrogen and room temperature. Uptake stops after 2 hours. After 4 hours the catalyst is filtered off and the filtrate is concentrated in vacuo to a solid. This material is triturated with ether, filtered and dried to afford a solid, m.p. s 237°, 241° C. dec, of cis-4-(2-aminophenoxy)-1-methyl-3-phenylpiperidine hydrochloride.

Analysis: Calculated for $C_{18}H_{22}N_2O$.HCl: 67.80%C; 7.27%H; 8.79%N; 11.12%Cl. Found: 67.79%C; 7.13%H; 8.49%N; 11.19%Cl.

EXAMPLE 14

Trans-1-methyl-4-(2-nitrophenoxy)-3-phenylpiperidine hydrochloride

The procedure of Example 12 is repeated except for the following. After the material is chromatographed on silica gel, using acetone, then 25% and finally 50% methanol/acetone solution as solvent, a purified trans isomer is obtained as the free base. The hydrochloride salt is formed by dissolving the free base in dichloromethane and treating with an HCl-saturated ether solution. The solvent is removed in vacuo and the resulting solid is triturated with ether and filtered to afford a solid, m.p. s 223°, 231.5°–233° C., of trans-1-methyl-4-(2-nitrophenoxy)-3-phenylpiperidine hydrochloride.

Analysis: Calculated for $C_{18}H_{20}N_2O_3$.HCl: 61.97%C; 6.07%H; 8.03%N; 10.17%Cl. Found: 61.94%C; 5.79%H; 8.13%N; 9.87%Cl.

EXAMPLE 15

Trans-4-(2-aminophenoxy)-1-methyl-3-phenylpiperidine oxalate

A solution of 3.94 g of trans-1-methyl-4-(2-nitrophenoxy)-3-phenylpiperidine hydrochloride, of Example 14, in a mixture of 100 ml of 190 proof ethanol and 25 ml of distilled water is hydrogenated at 45 psi and room temperature over 0.39 g of palladium on carbon catalyst. Hydrogen uptake stops after 2.5 hours. After 4.5 hours, the catalyst is filtered off and the filtrate is concentrated in vacuo to an oil which crystallizes under high vacuum. The resulting solid is triturated with ether, filtered and dried to afford a solid which melts at approximately 100° C. even after extensive drying in vacuo over $P_2O_5$ at 80° C. The free base of the product is generated. An oil is obtained. This material is dissolved in ether and added dropwise to a solution of 0.92 g of oxalic acid in ether. The resulting solid is filtered, washed with ether and dried briefly in vacuo to afford a solid which partially melts at 50° C. Trituration with boiling ethanol causes transformation first to a gum and then to a solid. The mixture is cooled to room temperature and left to stand 18 hours, then the solid is filtered, washed with cold ethanol, then ether and dried to afford a solid, m.p. 184°–186° C. dec., of trans-4-(2-aminophenoxy)-1-methyl-3-phenylpiperidine oxalate.

Analysis: Calculated for $C_{18}H_{22}N_2O.(CO_2H)_2$: 64.50%C; 6.50%H; 7.52%N. Found: 64.37%C; 6.33%H; 7.43%N.

EXAMPLE 16

Trans-1-methyl-4-(3-nitrophenoxy)-3-phenylpiperidine hydrochloride

A mixture of 1.2 g of sodium hydride, 50 ml of dry DMF and 7.65 g of trans-1-methyl-3-phenyl-4-piperidinol (free base of Example 1) is briefly heated to 120° C. under nitrogen, then cooled to room temperature. A solution of 7.06 g of 1-fluoro-3-nitro benzene in 25 ml of DMF is added dropwise over a 10-minute period. The pot temperature rises to 45° C. and begins to decline immediately after completion of the addition. After 72 hours at room temperature under nitrogen, the mixture is partitioned between saturated aqueous NaCl solution and ether. The aqueous phase is extracted with ether and the combined ether extracts are washed with water. The ether is removed in vacuo and the resulting oil is dissolved in dichloromethane and extracted with 2 N HCl solution. The organic phase is washed with 10% aqueous NaOH solution and saturated aqueous NaCl solution, dried over anhydrous $Na_2SO_4$, filtered, and concentrated in vacuo to afford an oil. Upon dissolving this oil in an ether-hexane mixture a solid begins to precipitate out. After allowing the mixture to stand at room temperature for two hours, the mixture is filtered and the filtrate is concentrated to an oil. This oil is dissolved in ether and the hydrochloride is formed by addition of an HCl-saturated ether solution. The resulting solid is filtered and washed with ether to afford a solid, mp s 229°, 231°–234° C. Recrystallization twice from isopropanol affords crystals, of trans-1-methyl-4-(3-nitrophenoxy)-3-phenylpiperidine hydrochloride, mp s 239.5, 241°–243° C.

Analysis: Calculated for $C_{18}H_{20}N_2O_3.HCl$: 61.97%C; 6.07%H; 8.03%N; 10.17%Cl. Found: 62.05%C; 6.06%H; 8.06%N; 10.21%Cl.

EXAMPLE 17

Trans-4-(3-aminophenoxy)-1-methyl-3-phenylpiperidine

A solution of 4.2 g of trans-1-methyl-4-(3-nitrophenoxy)-3-phenylpiperidine hydrochloride of Example 16, in a mixture of 100 ml of 190 proof ethanol and 25 ml of distilled water is hydrogenated over 0.42 g of 10% palladium on carbon catalyst at 45 psi of hydrogen and room temperature. After 3 hours and 15 minutes the mixture is filtered and the filtrate is concentrated in vacuo to a colorless foam which is triturated with ether, filtered and dried to afford a solid material which has an approximate melting point of 115°–130° C. The free base is generated by dissolving the salt in dichloromethane and washing with 10% aqueous NaOH solution. An oil is thus obtained. Trituration of this oil with a minimum of ether affords a colorless solid, mp s 90°, 91°–93° C., of trans-4-(3-aminophenoxy)-1-methyl-3-phenylpiperidine.

Analysis: Calculated for $C_{18}H_{22}N_2O$: 76.56%C; 7.85%H; 9.92%N. Found: 76.41%C; 7.81%H; 9.79%N.

EXAMPLE 18

Cis-1-methyl-4-(3-nitrophenoxy)-3-phenylpiperidine hydrochloride

A mixture of 6.8 g of 1-methyl-3-phenyl-4-piperidinol (a mixture of isomers, predominately cis of Example 1), 1.08 g of sodium hydride and 50 ml of DMF is briefly heated to 120° C. under nitrogen, then cooled to 5° C. in an ice water bath. The bath is then removed and a solution of 6.35 g of 1-fluoro-3-nitrobenzene in 25 ml of DMF is added dropwise over a 15-minute period. The mixture is stirred 18 hours at room temperature, then partitioned between saturated aqueous NaCl solution and ether. The aqueous phase is extracted again with ether, and the combined ether extracts are then washed with water and saturated aqueous NaCl solution and concentrated in vacuo to an oil. This oil is taken up in dichloromethane and is extracted with 2 N HCl solution. The dichloromethane phase is washed with 10% aqueous NaOH solution, then with saturated aqueous NaCl solution, dried over $Na_2SO_4$ and concentrated in vacuo to afford an oil which is taken up in a mixture of ether and hexane. After standing 18 hours a precipitate is filtered off and the filtrate is concentrated in vacuo to afford an oil. This oil is chromatographed on silica gel, using acetone and then 25% acetone/methanol as solvent. Pure trans and pure cis isomers are thus obtained. The cis isomer (as an oil) is taken up in dichloromethane and treated with an HCl saturated ether solution. The solvent is removed in vacuo. Trituration of the resulting foam with ether causes a solidification to occur to afford a crude solid, mp s 187°, 192°–200° C. Recrystallization from acetone/ethyl acetate affords crystals, mp s 199°, 201°–204.5° C. of cis-1-methyl-4-(3-nitrophenoxy)-3-phenyl piperidine hydrochloride.

Analysis: Calculated for $C_{18}H_{20}N_2O_3.HCl$: 61.97%C; 6.07%H; 8.03%N; 10.17%Cl. Found 62.02%C; 5.94%H; 8.12%N; 10.07%Cl.

EXAMPLE 19

Cis-4-(3-aminophenoxy)-1-methyl-3-phenylpiperidine hydrochloride

A solution of 4.6 g of cis-1-methyl-4-(3-nitrophenoxy)-3-phenylpiperidine hydrochloride of Example 18, in 110 ml of 190 proof ethanol is hydrogenated at 45 psi of hydrogen and room temperature over 0.46 g of 10% palladium on carbon catalyst. Hydrogen uptake stops after 2.5 hours. The catalyst is filtered off, and the filtrate is concentrated in vacuo to afford a foam which solidifies upon trituration with ether to afford a crude solid, mp s 232°, 249.5° C. dec, This material is recrystallized from absolute ethanol by boiling the filtered solution down, cooling, filtering and washing with absolute ethanol and then ether to yield cis-4-(3-aminophenoxy)-1-methyl-3-phenylpiperidine hydrochloride, mp 259°–260.5° C.

Analysis: Calculated for $C_{18}H_{22}N_2O \cdot HCl$: 67.80%C; 7.27%H; 8.79%N; 11.12%Cl. Found: 67.78%C; 7.18%H; 8.96%N; 10.88%Cl.

EXAMPLE 20 a.
Trans-1-ethoxycarbonyl-3-phenyl-4-(4-trifluoromethylphenoxy)piperidine 1.57 ml of ethyl chloroformate are added, with stirring under nitrogen to a mixture of 5.0 g of trans-1-methyl-3-phenyl-4-(4-trifluoromethylphenoxy)piperidine (free base of Example 1), 2.06 g of anhydrous potassium carbonate and 30 ml of anhydrous benzene. After 15 minutes at room temperature the mixture is kept at 70° C. for 18 hours. Another 0.4 ml of ethyl chloroformate is added, and the mixture is refluxed for 18 hours, and then allowed to stir an additional 24 hours at room temperature. The reaction mixture is then poured into a mixture of ethyl acetate, water; and saturated aqueous NaCl solution. The phases are separated and the aqueous phase is extracted with ethyl acetate. The combined organic extracts are dried over anhydrous $Na_2SO_4$ and then concentrated in vacuo to a gum. Trituration of this material with an ether-petroleum ether mixture gives a small amount of a solid. Concentration of the filtrate in vacuo affords an oil of trans-1-ethoxycarbonyl-3-phenyl-4-(4-trifluoromethylphenoxy)piperidine.

Analysis: Calculated for $C_{21}H_{22}F_3NO_3$: 64.11%C; 5.64%H; 3.56%N; 14.49%F. Found: 64.22%C; 5.07%H; 3.47%N; 14.23%F.

b.
Trans-3-phenyl-4-(4-trifluoromethylphenoxy)piperidine

A mixture of 4.51 g of trans-1-ethoxycarbonyl-3-phenoxy-4-(4-trifluoromethylphenoxy)piperidine, 60 ml of absolute ethanol and 30 ml of 20% aqueous NaOH solution is refluxed 18 hours under nitrogen. The ethanol is then removed in vacuo, and the aqueous residue is partitioned between water and dichloromethane. The aqueous phase is extracted with dichloromethane. The organic extracts are dried over anhydrous $Na_2SO_4$ and then concentrated in vacuo to an oil which crystallizes under high vacuum. Recrystallization from hexane yields a crystalline solid, mp s 76°, 77°–79° C. of trans-3-phenyl-4-(4-trifluoromethylphenoxy)piperidine.

Analysis: Calculated for $C_{18}H_{18}F_3NO$: 67.28%C; 5.65%H; 4.36%N. Found: 67.50%C; 5.78%H; 4.30%N.

EXAMPLE 21 a.
Trans-1-(3-p-fluorobenzoyl)propyl-3-phenyl-4-(4-trifluoromethylphenoxy)piperidine ethylene ketal maleate A mixture of 3.42 g of trans-3-phenyl-4-(4-trifluoromethylphenoxy)piperidine of Example 20, 2.05 g of sodium bicarbonate, 2.05 g of potassium iodide, 2.99 g of γ-chloro-p-fluorobutyrophenone ethylene ketal and 50 ml of dry DMF are stirred 18 hours at 90° C. under nitrogen. The mixture is cooled and is partitioned between a mixture of ether and water. The aqueous phase is extracted with ether, and the combined ether extracts are washed with water and then dried over anhydrous $Na_2SO_4$. Concentration in vacuo affords a gum which is taken up in boiling hexane (approximately 250 ml) and filtered to remove insoluble residue. Removal of the solvent in vacuo affords a crude ketal as a gum. A portion of this material is chromatographed over silica gel, using chloroform, 1% and finally 2% methanol/chloroform as solvent. The purest fraction (the free base) is dissolved in ether and treated with a solution of 0.1 g maleic acid in 10 ml of ether. The resulting precipitate is filtered, washed with ether, and recrystallized from toluene to afford a solid, m.p. s 162°, 163.5°–165.5° C., of trans-1-(3-p-fluorobenzoyl)propyl-4-(4-trifluoromethylphenoxy)piperidine ethylene ketal maleate.

Analysis: Calculated for $C_{30}H_{31}F_4NO_3 \cdot C_4H_4O_4$: 63.25%C; 5.46%H; 11.77%F; 2.17%N. Found: 63.34%C; 5.47%H; 11.61%F; 1.95%N.

b.
Trans-1-(3-p-fluorobenzoyl)propyl-3-phenyl-4-(4-trifluoromethylphenoxy)piperidine maleate 4.42 g of the free base of Example 21a above is taken up in 10 ml of 2 N HCl solution and stirred 18 hours at room temperature. The mixture is basified with 25 ml of 10% aqueous NaOH solution and is extracted with ether. The combined ether extracts are washed with 100 ml of saturated aqueous NaCl solution, dried over anhydrous $MgSO_4$, and concentrated in vacuo to an oil. This material is dissolved in 100 ml of boiling hexane, filtered to remove undissolved material, and concentrated in vacuo to an oil. A portion of the oil is dissolved in about 100 ml of ether and treated with a solution of 0.87 g of maleic acid in 100 ml of ether. The resulting precipitate is filtered, washed with ether and dried to afford a solid, m.p. s 106°, 115°–118° C. This material is suspended in 50 ml of boiling ether, and toluene is added until the boiling mixture becomes a solution. Cooling and scratching causes crystallization to occur. The recrystallized solid is filtered, washed with ether and dried to afford a solid, m.p. s 137.5°, 139.5°–141.5° C., of trans-1-(3-p-fluorobenzoyl)propyl-3-phenyl-4-(4-trifluoromethylphenoxy)piperidine maleate.

Analysis: Calculated for $C_{28}H_{27}F_4NO_2 \cdot C_4H_4O_4$: 63.89%C; 5.19%H; 2.33%N; 12.63%F. Found: 63.92%C; 5.09%H; 1.99%N; 12.42%F.

EXAMPLE 22 a. Cis-1-methyl-3-phenyl-4-piperidinol

The procedure of Example 1a. through 1e. is repeated. 25 ml of a 1.0 M solution of lithium tri-second-ary-butylborohydride in THF are added dropwise over a 10-minute period to a solution of 3.79 g of 1-methyl-3-phenyl-4-piperidone and 20 ml of tetrahydrofuran (THF) (distilled over lithium aluminum hydride), maintained at 0° C. The mixture gradually warms to 15° C. after two hours of stirring and an additional 5 ml of borohydride reagent are added and the mixture is stirred 18 hours at room temperature under a nitrogen atmosphere. The mixture is then treated with 90 ml of 10 weight percent aqueous NaOH solution followed by 61 ml of 30 percent by weight aqueous $H_2O_2$ solution. The mixture is stirred for 18 hours at room temperature under a nitrogen atmosphere and is then extracted with ether and then $CH_2Cl_2$. The organic extracts are combined and washed with saturated aqueous NaCl solution and dried over $Na_2SO_4$. The organic extracts are then filtered and concentrated in vacuo to a solid. The solid is triturated with petroleum ether, filtered and dried for 3 hours at 60° C. over $P_2O_5$. The solid product of cis-1-methyl-3-phenyl-4-piperidinol has a melting point s 127° C., 131°–133° C.

Analysis: Calculated for $C_{12}H_{17}NO$: 75.35%C; 8.96%H; 7.32%N. Found: 75.24%C; 8.96%H; 7.39%N.

b.
Cis-1-methyl-3-phenyl-4-(4-trifluoromethylphenoxy)-piperidine hydrochloride

A suspension of 9.56 g of cis-1-methyl-3-phenyl-4-piperidinol, Example 22a above, in 100 ml of benzene is added to a suspension of 1.32 g of sodium hydride in 50 ml of dry benzene. The mixture is heated to reflux, and 50 ml of dry DMF are added in portions over a two hour period. The solution is cooled to 13° C. and a solution of 12.31 g of p-fluorobenzotrifluoride in 50 ml of benzene is added all at once. A slight rise in temperature occurs. After stirring at room temperature under nitrogen for 48 hours, the reaction mixture is poured into a mixture of ether and aqueous NaCl solution. The aqueous phase is extracted with ether, and the combined ether extracts are dried over anhydrous $Na_2SO_4$ and concentrated in vacuo to a mixture of an oil and a solid. This material is dissolved in 250 ml of boiling hexane and gravity-filtered to remove insoluble material. The cool filtrate is re-filtered to remove additional impurities, and then is reduced in volume. Scratching causes crystallization of a solid. An oil from the filtrate is separated out by dissolving the oil in dichloromethane and washing with 2 N HCl solution. The dichloromethane phase is washed with 20% aqueous NaOH solution (to liberate the free base of the product), dried over anhydrous $Na_2SO_4$, and concentrated in vacuo to an oil (free base). This material is dissolved in ether, filtered, and is then added to a stirred solution of ether saturated with dry HCl gas. The solvent is removed in vacuo and trituration of the residue with an ether causes solidification to occur to yield cis-1-methyl-3-phenyl-4-(4-trifluoromethylphenoxy)piperidine hydrochloride. Recrystallization from toluene affords solid product, mp s 175°, 177.5°–179.5° C.

Analysis: Calculated for $C_{19}H_{20}F_3NO.HCl$: 61.37%C; 5.69%H; 3.77%N; 9.54%Cl. Found: 61.36%C; 5.63%H; 3.79%N; 9.55%Cl.

EXAMPLE 23 a.
Cis-3-phenyl-1-(2,2,2-trichloroethoxycarbonyl)-4-(4-trifluoromethylphenoxy)piperidine 0.46 g of anhydrous potassium carbonate and 0.5 ml of 2,2,2-trichloroethyl chloroformate are added under nitrogen to a solution of 1.11 g of the free base of cis-1-methyl-3-phenyl-4-(4-trifluoromethylphenoxy)piperidine of Example 22 in 10 ml of dry benzene. After 1 hour at room temperature the mixture is refluxed 18 hours. Another 0.045 ml of 2,2,2-trichloroethyl chloroformate is added, the mixture is again refluxed 18 hours, then cooled and partitioned between ether and water. The organic phase is washed with saturated aqueous NaCl solution, dried over anhydrous $Na_2SO_4$, and concentrated in vacuo to an oil. This material is dissolved in benzene and filtered through a column of silica gel, then is further purified by preparative chromatography on five 2 mm silica preparative plates, using 3:1 petroleum ether as solvent. A nearly colorless glass of cis-3-phenyl-1-(2,2,2-trichloroethoxycarbonyl)-4-(4-trifluoromethylphenoxy)piperidine is obtained.

Analysis: Calculated for $C_{21}H_{19}Cl_3F_3NO_3$: 50.77%C; 3.86%H; 21.41%Cl; 2.82%N. Found: 50.95%C; 3.89%H; 21.52%Cl; 2.54%N.

b. Cis-3-phenyl-4-(4-trifluoromethylphenoxy)piperidine maleate

A mixture of 6.81 g of cis-3-phenyl-1-(2,2,2-trichloroethoxycarbonyl)-4-(4-trifluoromethylphenoxy)piperidine of Example 23a, 55 ml of glacial acetic acid, and 3.73 g of zinc dust is stirred at room temperature under nitrogen for 72 hours. The mixture is then filtered through Celite, and the cake is washed with ether and then water. The filtrate is basified with 10% aqueous NaOH solution and extracted with ether. The ether extracts are dried over anhydrous $MgSO_4$ and concentrated in vacuo to a gum. This material is taken up in boiling hexane and filtered to remove undissolved residue. The cooled liquid is refiltered and then concentrated in vacuo to a gum which crystallizes on standing. This material is dissolved in ether and is treated with a solution of 1.28 g of maleic acid in approximately 125 ml of ether. The resulting solid is washed with ether and dried to afford a product, m.p. s 145.5°, 146.5°–148.5° C., of cis-3-phenyl-4-(4-trifluoromethylphenoxy)piperidine maleate.

Analysis: Calculated for $C_{18}H_{18}F_4NO.C_4H_4O_4$: 60.41%C; 5.07%H; 3.20%N; 13.03%F. Found: 60.55%C; 5.06%H; 3.17%N; 12.97%F.

EXAMPLE 24

Trans-4-(4-methoxyphenoxy)-1-methyl-3-phenylpiperidine hydrochloride

A solution of 4.35 g of diethylazodicarboxylate in 100 ml of THF is added dropwise under nitrogen over a 7-hour period to a solution of 4.78 g of cis-1-methyl-3-phenyl-4-piperidinol of Example 22, 6.56 g of triphenylphosphine and 3.1 g of p-methoxyphenol in 100 ml of dry THF. After stirring 18 hours at room temperature, the solvent is removed in vacuo and the residue is triturated with a mixture of ether and hexane. The solids are filtered off, washed with hexane, and discarded. The filtrate is concentrated in vacuo to an oil. This material is taken up in dichloromethane and washed with aqueous 2 N HCl solution, then with 10% aqueous NaOH solution, water, and saturated aqueous NaCl solution. After drying over anhydrous $Na_2SO_4$ the solvent is removed in vacuo to give an oil, from which some solid is obtained upon trituration with hexane. The solid is filtered off, washed with hexane, and discarded. The filtrate is concentrated in vacuo to an oil. This material is chromatographed on silica gel using acetone as solvent. The purified product is obtained as an oil which crystallizes upon standing (m.p. 70°–73° C.). This material is dissolved in ether and added dropwise with stirring under nitrogen to an HCl saturated ether solution. The solvent is removed in vacuo. Trituration of the the resulting gum with ether causes solidification to occur. The solid is filtered, washed with ether, and dried to afford trans-4-(4-methoxyphenoxy)-1-methyl-3-phenylpiperidine hydrochloride, mp s 215°, 225°-227° C. Recrystallization from acetone-ethyl acetate gives a crystalline solid which has mixed mp s 228° C., 229.5°-230.5° C.

Analysis: Calculated for $C_{19}H_{23}NO_2 \cdot HCl$: 68.35%C; 7.25%H; 4.20%N; 10.62%Cl. Found: 68.10%C; 7.06%H; 4.07%N; 10.81%Cl.

EXAMPLE 25

Trans-1-methyl-4-phenoxy-3-phenylpiperidine oxalate

A mixture of 10.7 g of 1-methyl-3-phenyl-4-piperidinol (mixture of isomers) of Example 1, 1.68 g of sodium hydride and 35 ml dry DMF is heated at approximately 80° C. for about one hour (until no solid remained) under nitrogen. The solution is then cooled to room temperature, and another 100 ml of dry DMF are added, followed by 20 ml of fluorobenzene. After heating the mixture for 18 hours at approximately 72° C. under nitrogen, another 20 ml of fluorobenzene are added and the reaction mixture is allowed to continue at this temperature for another 48 hours. The mixture is then cooled and poured into 500 ml of saturated aqueous NaCl solution, and extracted with ether. The combined ether extracts are washed with water and saturated aqueous NaCl solution, dried over anhydrous MgSO$_4$, and concentrated in vacuo to an oil which solidifies under high vacuum. This material is triturated with hexane, and the undissolved solid is filtered off. The filtrate is concentrated in vacuo to an oil, which is taken up in dichloromethane and washed with 2 N HCl. The CH$_2$Cl$_2$ phase is then washed with 10% aqueous NaOH solution and saturated aqueous NaCl solution, dried over anhydrous MgSO$_4$ and concentrated in vacuo to afford an oil. This material is chromatographed on silica gel, using acetone as solvent to yield a purified free base. This material is dissolved in ether, filtered to remove insoluble material, and added dropwise to a solution of 0.46 g of oxalic acid in 25 ml of ether. The resulting precipitate is filtered, washed with ether, and dried to afford trans-1-methyl-4-phenoxy-3-phenylpiperidine oxalate, mp s 166° C., 175°-176° C., dec. Recrystallization from acetone affords a crystalline product, mp s 168°, 170°-171.5° C., dec.

Analysis: Calculated for $C_{18}H_{21}NO \cdot (CO_2H)_2$: 67.21%C; 6.49%H; 3.92%N. Found: 67.31%C; 6.55%H; 3.73%N.

EXAMPLE 26

Trans-4-(4-chlorophenoxy)-1-methyl-3-phenylpiperidine

A suspension of 7.65 g of 1-methyl-3-phenyl-4-piperidinol (approximately a 50:50 mixture of isomers) of Example 1 in 100 ml of benzene is added to a suspension of 1.2 g of sodium hydride in 50 ml dry benzene. The mixture is heated to reflux, and 25 ml of dry DMF are added dropwise over a 10-minute period. After refluxing for 1 hour, the mixture is cooled to room temperature and a solution of 6.53 g of p-chlorofluorobenzene in 50 ml of benzene is added all at once. After stirring for 18 hours at room temperature, 100 ml of DMF are added and the mixture is refluxed for 5 hours, then stirred for 18 hours at room temperature and then refluxed an additional 4 hours. The mixture is partitioned between ether and saturated aqueous NaCl solution. The aqueous phase is extracted with ether. The combined extracts are washed with water, saturated aqueous NaCl solution and dried over anhydrous MgSO$_4$. Removal of the solvent in vacuo affords an oil. This material is dissolved in dichloromethane and extracted with 2 N HCl solution. The dichloromethane phase is washed with saturated aqueous NaHCO$_3$ solution, dried over anhydrous MgSO$_4$, filtered and concentrated in vacuo to afford an oil which crystallizes on standing. This material is chromatographed on silica gel, using acetone and then 25% methanol/acetone as solvent. A pure product, trans-4-(4-chlorophenoxy)-1-methyl-3-phenylpiperidine, is thus obtained, m.p. s 83.5°, 84.5°-87° C.

Analysis: Calculated for $C_{18}H_{20}ClNO$: 71.63%C; 6.68%H; 11.75%Cl; 4.64%N. Found: 71.39%C; 6.61%; 11.92%Cl; 4.41%N.

EXAMPLE 27

Trans-1-methyl-3-phenyl-4-(4-tolyloxy)piperidine maleate

A mixture of 4.78 g of cis-1-methyl-3-phenyl-4-piperidinol of Example 22, 7.21 g of triphenylphosphine, 2.97 g of p-cresol and 125 ml of anhydrous benzene is cooled to 6° C. and a solution of 4.79 g of diethyl azodicarboxylate in 125 ml of benzene is added dropwise under nitrogen over a 90-minute period. The temperature is allowed to rise gradually so that at completion of the addition it is 22° C. After stirring for 18 hours at room temperature, the suspended solid is filtered off, washed with hexane, and the filtrate concentrated in vacuo to an oil. This material is triturated with 200 ml of hexane for 90 minutes, the liquid is decanted, and the solid triturated for a few minutes with another 200 ml of hexane. Concentration in vacuo of the hexane extracts affords an oil, which is dissolved in 250 ml of dichloromethane and extracted with 2 N HCl solution. The dichloromethane phase is washed successively with 10% aqueous NaOH solution, water, and saturated aqueous NaCl solution, dried over anhydrous Na$_2$SO$_4$, filtered and concentrated in vacuo to a mixture of a solid and an oil. This mixture is triturated with hexane, filtered, and the filtrate is concentrated in vacuo to afford an oil. This oil is chromatographed on silica gel, using acetone and then 25% methanol/acetone as solvent. The fractions containing product are combined and concentrated in vacuo to an oil which is taken up in ether and filtered through a Celite pad. The filtrate affords an oil which is triturated with boiling hexane and filtered hot. The filtrate is cooled and the resultant precipitated solid is filtered off and the filtrate concentrated in vacuo to yield an oil. This oil is dissolved in 50 ml of ether and added dropswise to a solution of 1.36 g of maleic acid in 25 ml of ether. The resulting solid is filtered, washed with ether, and dried to afford crude salt, melting near 100° C. Recrystallization from ethyl acetate affords a solid of trans-1-methyl-3-phenyl-4-(4-tolyl)piperidine maleate, mp s 130°, 131°-132° C.

Analysis: Calculated for $C_{19}H_{23}NO \cdot C_4H_4O_4$: 69.50%C; 6.85%H; 3.52%N. Found: 69.31%C; 6.86%H; 3.26%N.

EXAMPLE 28 a.

Trans-4-(4-chlorophenoxy)-1-ethoxycarbonyl-3-phenylpiperidine

A mixture of 10.26 g of trans-4-(4-chlorophenoxy)-1-methyl-3-phenylpiperidine of Example 26, 7.05 g of anhydrous potassium carbonate, 75 ml of dry benzene and 5.53 g of ethyl chloroformate is refluxed for 18 hours under nitrogen. The mixture is then partitioned between distilled water and hexane. The organic phase is washed with water, the combined aqueous extracts are extracted with hexane, the combined organic extracts are washed with saturated aqueous NaCl solution, dried over anhydrous MgSO$_4$, and concentrated in vacuo to afford an oil which almost completely crystallizes after standing for about 64 hours. The colorless solid is triturated with hexane, filtered and washed well with hexane to afford trans-4-(4-chlorophenoxy)-1-ethoxycarbonyl-3-phenylpiperidine, m.p. s 80°, 81.5°–84° C.

Analysis: Calculated for C$_{20}$H$_{22}$ClNO$_3$: 66.75%C; 6.16%H; 9.85%Cl; 3.89%N. Found: 66.71%C; 6.14%H; 9.83%Cl; 3.82%N.

b. Trans-4-(4-chlorophenoxy)-3-phenylpiperidine

A mixture of 8.78 g of trans-4-(4-chlorophenoxy)-1-ethoxycarbonyl-3-phenylpiperidine, 64 ml of 20% aqueous NaOH solution and 125 ml of absolute ethanol is refluxed for 18 hours under nitrogen. The ethanol is then removed in vacuo and the aqueous residue is partitioned between dichloromethane and distilled water. The aqueous phase is extracted with dichloromethane, and the combined organic extracts are then washed with water, saturated aqueous NaCl solution, dried over anhydrous Na$_2$SO$_4$ and concentrated in vacuo to afford a solid which is recrystallized from cyclohexane to yield trans-4-(4-chlorophenoxy)-3-phenylpiperidine, mp 101.5°–103° C.

Analysis: Calculated for C$_{17}$H$_{18}$ClNO: 70.95%C; 6.30%H; 4.87%N; 12.32%Cl. Found: 70.87%C; 6.32%H; 4.64%N; 12.14%Cl.

EXAMPLE 29 a. Trans-4-(4-chlorophenoxy)-3-phenyl-1-phenylacetylpiperidine

A solution of 2.0 ml of phenylacetyl chloride in 50 ml of chloroform is added dropwise under nitrogen over a 20-minute period to a solution of 3.9 g of trans-4-(4-chlorophenoxy)-3-phenylpiperidine of Example 28 in 100 ml of dry chloroform containing 2.1 ml of triethylamine. The pot temperature reaches a maximum of 30° C. After 90 minutes, the chloroform solution is washed successively with water, 10% aqueous NaOH solution, water and saturated aqueous NaCl solution, dried over anhydrous Na$_2$SO$_4$, and concentrated in vacuo to an oil. Upon standing for 72 hours a single large crystal forms. 25 ml of hexane are added, and the oil is triturated as ether is slowly added. This procedure causes rapid crystallization of the oil. Approximately 50 ml of ether are added altogether. After standing at room temperature for 3 hours, the mixture is cooled for 2.5 hours in ice water, and the crystallized solid is filtered off and washed with hexane to afford a solid, m.p. s 93°, 93.5°–95.5° C., of trans-4-(4-chlorophenoxy)-3-phenyl-1-phenylacetylpiperidine.

Analysis: Calculated for C$_{25}$H$_{24}$ClNO$_2$: 73.97%C; 5.96%H; 3.45%N; 8.74% Cl. Found: 73.73%C; 5.96%H; 3.14%N; 8.79%Cl.

b. Trans-4-(4-chlorophenoxy)-1-phenethyl-3-phenylpiperidine hydrochloride 19 ml of a 1.0 M borane in THF solution are cooled to 2° C. under nitrogen, and a solution of 4.54 g of trans-4-(4-chlorophenoxy)-3-phenyl-1-phenylacetylpiperidine in 25 ml of dry THF is added dropwise over a 10-minute period, keeping the pot temperature below 5° C. After completing the addition, the mixture is refluxed for 60 minutes, then cooled and treated with 15 ml of 6 N HCl solution. The mixture is then heated and the THF distilled off at atmospheric pressure over a 50 minute period, at which point pot temperature is 90° C. and the head temperature 77° C. The aqueous residue is cooled, 100 ml of dichloromethane are added, and the mixture is basified with 50 ml of 10% aqueous NaOH solution. 100 ml of water are then added, and the phases are separated. The aqueous phase is extracted with dichloromethane. The combined dichloromethane extracts are washed successively with water and saturated aqueous NaCl solution, dried over anhydrous Na$_2$SO$_4$ and concentrated in vacuo to an oil. This material is dissolved in ether and redried over anhydrous MgSO$_4$, filtered and concentrated in vacuo to afford an oil. The oil is redissolved in ether and the hydrochloride is formed by addition of HCl-saturated ether solution. The solvent is removed in vacuo and the crude salt is triturated with ether and filtered to afford a solid, m.p. s 224° C., 233°–236° C. Recrystallization from acetone affords crystals of trans-4-(4-chlorophenoxy)-1-phenethyl-3-phenylpiperidine hydrochloride, mp s 230°, 232.5°–235.5° C.

Analysis: Calculated for C$_{25}$H$_{26}$ClNO.HCl: 70.09%C; 6.35%H; 16.55%Cl; 3.27%N. Found: 69.89%C; 6.30%H; 16.60%Cl. 3.21%N.

EXAMPLE 30

Trans-4-(4-fluorophenoxy)-1-methyl-3-phenylpiperidine

A mixture of 0.6 g of sodium hydride, 3.83 g of sodium hydride, 3.83 g of trans-1-methyl-3-phenyl-4-piperidinol of Example 1 and 30 ml of anhydrous DMF is heated to 90° C. for 1.5 hours, then cooled to room temperature. A solution of 2.85 g of p-difluorobenzene in 20 ml of DMF is added all at once; the mixture is stirred at 70°–80° C. under nitrogen for 48 hours. The mixture is cooled and partitioned between ether and saturated aqueous NaCl solution. The aqueous phase is extracted with ether, and the combined ether extracts are washed with water and saturated aqueous NaCl solution and then concentrated in vacuo to an oil. This material is dissolved in 200 ml of dichloromethane, and the solution is extracted with 2 N HCl solution. The dichloromethane phase is successively washed with 10% aqueous NaOH solution, water, saturated aqueous NaCl solution, dried over anhydrous Na$_2$SO$_4$, and concentrated in vacuo to afford an oil which crystallizes upon standing. This material is chromatographed on silica gel, using acetone and then 25% methanol/acetone as solvent to obtain trans-4-(4-fluorophenoxy)-1-methyl-3-phenylpiperidine, m.p. s 67°, 69.5°–71.5° C.

Analysis: Calculated for C$_{18}$H$_{20}$FNO: 75.76%C; 7.07%H; 4.91%N; 6.66%F. Found: 75.62%C; 7.00%H; 4.54%N; 6.49%F.

EXAMPLE 31

Cis-4-(4-acetamidophenoxy)-1-methyl-3-phenylpiperidine

A solution of 1.4 ml of acetyl chloride in 75 ml of chloroform is added dropwise under nitrogen over a 15-minute period to a solution of 5.05 g of the free base of cis-4-(4-aminophenoxy)-1-methyl-3-phenylpiperidine of Example 8 in 150 ml of dry chloroform containing 2.74 ml of triethylamine. The pot temperature reaches a maximum of 28° C. The reaction is complete in 30 minutes. The chloroform solution is washed with 10% aqueous NaOH solution, then with saturated aqueous NaCl solution, dried over anhydrous $Na_2SO_4$ and concentrated in vacuo to a foam which solidifies upon trituration with hexane. The hexane mixture is briefly heated to boiling, then cooled to room temperature and allowed to stand for 30 minutes before filtering. A crude solid results, mp s 172°, 173°–175° C. Recrystallization from toluene affords cis-4-(4-acetamidophenoxy)-1-methyl-3-phenylpiperidine, mp 174.5°–176.5° C.

Analysis: Calculated for $C_{20}H_{24}N_2O_2$: 74.04%C; 7.46%H; 8.64%N. Found: 74.21%C; 7.66%H; 8.69%N.

EXAMPLE 32

Trans-4-(3-chlorophenoxy)-1-methyl-3-phenylpiperidine hydrochloride

A mixture of 1.9 g of sodium hydride, 12.07 g of 1-methyl-3-phenyl-4-piperidinol (mixture of isomers of Example 1) and 70 ml. of dry DMF is heated at approximately 100° C. for 1 hour, under nitrogen, then cooled to room temperature. A solution of 16.45 g of 3-chlorofluorobenzene in 40 ml of DMF is added all at once, and the mixture is stirred for 18 hours at room temperature, then heated slowly so that after 4 hours the pot temperature is 68° C. After stirring for about 48 hours at room temperature, another 0.76 g of sodium hydride is added, and the mixture is again heated slowly to approximately 70° C. After 2 hours the mixture is cooled and treated with saturated aqueous NaCl solution, then poured into a mixture of saturated aqueous NaCl solution and ether. The phases are separated and the aqueous phase is extracted with ether. The combined ether extracts are washed with water, saturated aqueous NaCl solution, and concentrated in vacuo. The residue is partitioned between dichloromethane and water. The phases are separated, the aqueous phase is extracted with more dichloromethane, and the combined dichloromethane phases are extracted with 2 N HCl solution, then washed successively with 10% aqueous NaOH solution, water, saturated aqueous NaCl solution, and dried over anhydrous $Na_2SO_4$. Concentration in vacuo affords an oil which is a mixture of product isomers. This mixture is chromatographed on silica gel, using acetone as the initial solvent. The trans product is eluted with 25% methanol/acetone as solvent. The fractions containing the trans isomer are combined and concentrated in vacuo to an oil. This oil is taken up in ether, dried over anhydrous $Na_2SO_4$, filtered, and treated dropwise with HCl-saturated ether solution. The ether and excess HCl are removed in vacuo and the resuting gummy solid is triturated with fresh ether until completely solid. This solid is filtered, washed with ether and dried to afford a crude salt, mp s 211.5°, 213°–214.5° C. Recrystallization from acetone affords needles of trans-4-(3-chlorophenoxy)-1-methyl-3-phenylpiperidine hydrochloride having the same melting point.

Analysis: Calculated for $C_{18}H_{20}ClNO \cdot HCl$: 63.91%C; 6.26%H; 4.41%N; 20.96%Cl. Found: 63.92%C; 6.19%H; 4.10%N; 20.84%Cl.

EXAMPLE 33

Trans-4-(3-chlorophenoxy)-1-ethoxycarbonyl-3-phenylpiperidine 2.01 g of ethyl chloroformate are added to a mixture of 3.7 g of the free base of trans-4-(3-chlorophenoxy)-1-methyl-3-phenylpiperidine of Example 32, 2.56 g of anhydrous potassium carbonate, and 28 ml of dry benzene. The mixture is then refluxed for 18 hours under nitrogen. An additional 0.67 g of ethyl chloroformate is added, and, after 4 more hours of reflux, the mixture is cooled and partitioned between water and ether. The phases are separated and the aqueous phase is extracted with ether. The combined organic phases are washed with saturated aqueous NaCl solution, stirred for 18 hours with anhydrous $MgSO_4$, filtered and concentrated in vacuo to an oil comprising trans-4-(3-chlorophenoxy)-1-ethoxycarbonyl-3-phenylpiperidine.

Analysis: Calculated for $C_{20}H_{22}ClNO_3$: 66.75%C; 6.16%H; 3.89%N; 9.85%Cl. Found: 66.70%C; 6.36%H; 3.99%N; 9.41%Cl.

EXAMPLE 34

Trans-4-(3-chlorophenoxy)-3-phenylpiperidine hydrochloride

A mixture of 3.84 g of trans-4-(3-chlorophenoxy)-1-ethoxycarbonyl-3-phenylpiperidine of Example 33, 55 ml of absolute ethanol, and 28 ml of 10% aqueous NaOH solution is refluxed for 18 hours under nitrogen. The ethanol is then removed in vacuo and the aqueous residue is extracted with ether. The combined ether extracts are washed with saturated aqueous NaCl solution, dried over anhydrous $MgSO_4$, and concentrated in vacuo to an oil. This oil is dissolved in ether, filtered, and the filtrate treated with HCl-saturated ether solution until acidic to wet pH paper. The resulting precipitate is filtered, washed with ether and dried to afford a solid, m.p. 239°–241° C. Recrystallization from isopropanol affords crystals of trans-4-(3-chlorophenoxy)-3-phenylpiperidine hydrochloride, mp s 240°, 241.5°–243.5° C.

Analysis: Calculated for $C_{17}H_{18}ClNO \cdot HCl$: 62.97%C; 5.91%H; 4.32%N; 21.87%Cl. Found: 63.06%C; 6.06%H; 4.22%N; 21.86%Cl.

EXAMPLE 35

Cis-4-(4-chlorophenoxy)-1-methyl-3-phenylpiperidine oxalate

A mixture of 1.32 g of sodium hydride, 9.56 g of cis-1-methyl-3-phenyl-4-piperidinol of Example 22, 13.06 g of 4-chlorofluorobenzene and 75 ml of anhydrous DMF is stirred at room temperature under nitrogen for 144 hours, then for 18 hours at 50° C., and then again for 18 hours at 70° C. The mixture is cooled while treating with 250 ml of saturated aqueous NaCl solution, added to a mixture of ether and water, shaken, and the phases are separated. The aqueous phase is extracted with ether. The combined ether extracts are washed with saturated aqueous NaCl solution and concentrated in vacuo to a mixture of a solid and an oil. This mixture is triturated with ether and filtered, and the solid is washed with ether. The filtrate is concentrated in vacuo and the process is repeated. The filtrate is concentrated in vacuo to an oil, which is dissolved in dichloromethane and extracted with 2 N HCl solution. The dichloromethane phase is then washed with 10% aqueous NaOH solution and saturated aqueous NaCl solution, dried over anhydrous $Na_2SO_4$, and concentrated in vacuo to an oil. This material is taken up in hexane and decanted from an undissolved residue. The hexane filtrate is concentrated in vacuo to an oil which slowly crystallizes under high vacuum. NMR of this material shows it to be a mixture of approximately 77% title product and 23% of 1-methyl-3-phenyl-1,2,5,6-tetrahydropyridine. The maleate salt of this mixture is formed, but the maleate salt of the desired product does not solidify. However, the maleate salt of 1-methyl-3-phenyl-1,2,5,6-tetrahydropyridine is crystallized out of the mixture from an ether/ethyl acetate solution. The filtrate is concentrated in vacuo to a gum and the free base regenerated. The oxalate salt is then formed by dissolving the free base in 50 ml of ether and adding dropwise to a stirred solution of 0.65 g of oxalic acid in 50 ml of ether. The resulting gum partially solidifies during the addition and the remainder is solidified by trituration. In this manner a crude salt, m.p. s 132°, 142°–145° C., is obtained. This material is suspended in 150 ml of boiling ethyl acetate, and 35 ml of acetone are added. The solution is boiled down slightly, then filtered hot, the filtrate boiled down to a volume of about 75 ml, then filtered hot again. The cooled filtrate yields a colorless solid, m.p. 148.5°, 151.5° C. dec. of cis-4-(4-chlorophenoxy)-1-methyl-3-phenylpiperidine oxalate.

Analysis: Calculated for $C_{18}H_{20}ClNO \cdot C_2H_2O_4$: 61.30%C; 5.66%H; 3.58%N; 9.05%Cl. Found: 60.92%C; 5.52%H; 3.34%N; 8.87%Cl.

EXAMPLE 36

Cis-4-(3-chlorophenoxy)-1-methyl-3-phenylpiperidine hydrochloride

A mixture of 1.9 g of sodium hydride, 12.07 g of 1-methyl-3-phenyl-4-piperidinol (mixture of isomers) of Example 1 and 70 ml of dry DMF is heated at approximately 100° C. for 1 hour under nitrogen, then cooled to room temperature. A solution of 16.45 g of 3-chlorobenzene in 40 ml of DMF is added all at once, and the mixture is stirred for 18 hours at room temperature, then heated slowly so that after 4 hours the pot temperature is 68° C. After stirring for about 64 hours at room temperature, another 0.76 g of sodium hydride is added and the mixture is again heated slowly to approximately 70° C. After 2 hours the mixture is cooled and treated with 50 ml of saturated aqueous NaCl solution, then poured into a mixture of saturated aqueous NaCl solution and ether. The phases are separated and the aqueous phase is extracted with ether. The combined ether extracts are washed with water, saturated NaCl solution, and then concentrated in vacuo. The residue is partitioned between dichloromethane and water. The phases are separated and the aqueous phase is extracted with more dichloromethane. The combined dichloromethane phases are extracted with 2 N HCl solution, then washed successively with 10% aqueous NaOH solution, water, saturated aqueous NaCl solution, and dried over anhydrous $Na_2SO_4$. Concentration in vacuo affords an oil, with TLC shows to be a mixture of product isomers. This material is chromatographed on silica gel, using acetone as the initial solvent. The trans product is eluted with 25% methanol/acetone as solvent. The cis product is eluted with 25% and then 50% methanol/acetone, giving a crude free base which NMR shows to be an 8:3 mixture of cis product to 1-methyl-3-phenyl-1,2,5,6-tetrahydropyridine. The hydrochloride salt is prepared by dissolving the free base in ether and treating with HCl-saturated ether solution until the mixture is acidic to pH paper. The crude salt is filtered and washed with ether to afford a solid, m.p. s 180°, 207°–220° C. Recrystallization from acetone affords a solid of cis-4-(3-chlorophenoxy)-1-methyl-3-phenylpiperidine hydrochloride, mp s 230°, 231°–232.5° C.

Analysis: Calculated for $C_{18}H_{20}ClNO \cdot HCl$: 63.91%C; 6.26%H; 4.14%N; 20.96%Cl. Found: 63.81%C; 6.34%H; 3.99%N; 20.72%Cl.

EXAMPLE 37

Trans-1-methyl-3-phenyl-4-(3-tolyloxy)piperidine hydrochloride

A mixture of 4.78 g of cis-1-methyl-3-phenyl-4-piperidinol of Example 22, 7.21 g of triphenylphosphine, 2.97 g of m-cresol and 125 ml of dry benzene is cooled to 5° C. and treated dropwise under nitrogen over a 90 minute period with a solution of 4.79 g of diethyl azodicarboxylate in 125 ml of benzene. The pot temperature is 9° C. at completion of the addition. After stirring for 18 hours at room temperature the mixture is filtered and the solid is washed well with hexane. The filtrate is concentrated in vacuo to a gum. Trituration of this material with 250 ml of ether for 72 hours causes a solid to form. The solid is filtered off, triturated for 30 minutes with another 250 ml of hexane, filtered again, and the two filtrates are combined and concentrated in vacuo to an oil. This material is taken up in dichloromethane and extracted with 2 N HCl solution. The combined acid extracts are extracted with dichloromethane, and the combined dichloromethane phases are washed successively with 10% aqueous NaOH solution, water saturated aqueous NaCl solution, dried over anhydrous $Na_2SO_4$ and concentrated in vacuo to an oil which partially crystallizes upon standing. This material is stirred for 18 hours with hexane, then filtered, and the solid is washed well with hexane. The filtrate is concentrated in vacuo to give an oil. This material is chromatographed on silica gel, using acetone and then 25% methanol/acetone solution as solvent. A purified product is obtained as a nearly colorless oil which crystallizes upon standing. The hydrochloride salt is prepared by dissolving the free base in ether and treating the stirred solution dropwise with an HCl-saturated ether solution. A portion of crude salt is dissolved in a boiling mixture of 85 ml of acetone and 5 ml of methanol, the solution is filtered hot, and the filtrate boiled down to a volume of approximately 50 ml. A colorless solid, m.p. s 224.5°, 255.5°–227° C., of trans-1-methyl-3-phenyl-4-(3-tolyloxy)piperidine hydrochloride is obtained.

Analysis: Calculated for $C_{19}H_{23}NO \cdot HCl$: 71.79%C; 7.61%H; 11.16%Cl; 4.41%N. Found: 71.52%C; 7.65%H; 11.05%Cl; 4.30%N.

EXAMPLE 38

Trans-1-methyl-3-phenyl-4-(2-tolyloxy)piperidine hydrochloride

A mixture of 4.78 g of cis-1-methyl-3-phenyl-4-piperidinol of Example 22, 7.21 g of triphenylphosphine, 2.97 g of o-cresol and 125 ml of dry benzene is treated dropwise under nitrogen over a 90 minute period with a solution of 4.79 g of diethyl azodicarboxylate at room temperature. After stirring for 18 hours the solid is filtered off, washed well with hexane, and the filtrate concentrated in vacuo to an oil. After trituration of the oil for 18 hours with 250 ml of hexane, the undissolved material is filtered off, washed well with hexane and the filtrate concentrated in vacuo to oil. The oil is dissolved in 250 ml of ether and extracted with 2 N HCl solution. The salts of the basic components form an oil suspended in the aqueous phase. The combined acid extracts are then extracted with ethyl acetate. The ethyl acetate extracts are washed with 10% aqueous NaOH solution, then with saturated aqueous NaCl solution, dried over anhydrous $Na_2SO_4$, filtered and concentrated in vacuo to an oil. This material is chromatographed on silica gel, using acetone as solvent, to obtain a crude free base. This material is dissolved in ether and the solution is treated dropwise with an HCl-saturated ether solution. The crude hydrochloride of trans-1-methyl-3-phenyl-4-(2-tolyloxy)piperidine is filtered, washed with ether, and dried to afford a solid. This solid is suspended in boiling ethyl acetate. Gradual addition of acetone to the boiling mixture gives a solution. After filtering and boiling the filtrate down to a volume of 50 ml, crystallization begins. The crystalline salt is filtered, washed with ethyl acetate, then ether, and dried to afford a solid, m.p. s 211°, 222°–223° C., of trans-1-methyl-3-phenyl-4-(2-tolyloxy)piperidine hydrochloride.

Analysis: Calculated for $C_{19}H_{23}NO.HCl$: 71.79%C; 7.61%H; 11.16%Cl; 4.41%N. Found: 71.84%C; 7.70%H; 11.47%Cl; 4.15%N.

EXAMPLE 39

Cis-4-(4-cyanophenoxy)-1-methyl-3-phenylpiperidine

A mixture of 0.31 g of sodium hydride, 2.48 g of cis-1-methyl-3-phenyl-4-piperidinol of Example 22 and 20 ml of dry DMF is slowly heated to 80° C. When hydrogen evolution is no longer observed, the mixture is cooled to 3° C. and a solution of 1.73 g of p-fluorobenzonitrile in 10 ml of DMF is added. The mixture is stirred for 18 hours at room temperature under nitrogen, poured into 100 ml of distilled water, and extracted with chloroform. The chloroform extracts are dried over anhydrous $Na_2SO_4$ and concentrated in vacuo to an oil containing DMF. This oil is partitioned between saturated aqueous NaCl solution and ether. The aqueous phase is extracted with ether, and the ether extracts are then washed with water and dried over anhydrous $Na_2SO_4$. Concentration in vacuo affords an oil which crystallizes while under high vacuum. This material is chromatographed on silica gel, using 25% methanol-/acetone solution to obtain cis-4-(4-cyanophenoxy)-1-methyl-3-phenylpiperidine, m.p. s 138°, 139°–141° C.

Analysis: Calculated for $C_{19}H_{20}N_2O$: 78.05%C; 6.89%H; 9.58%N. Found: 78.27%C; 6.85%H; 9.57%N.

EXAMPLE 40

Trans-1-methyl-3-phenyl-4-phenylthiopiperidine hydrochloride

A suspension of 8.30 g of N-phenylthiophthalimide in 75 ml of dry benzene at room temperature under nitrogen is treated with 6.58 g of tri-n-butylphosphine. After 15 minutes a dark orange solution is obtained and 4.78 g of cis-1-methyl-3-phenyl-4-piperidinol of Example 22 are added all at once. After 5 minutes the solid dissolves. After stirring for 24 hours at room temperature, the resultant suspension is filtered and the solid is washed well with hexane. The filtrate is concentrated in vacuo to an oil which is triturated for 18 hours with 250 ml of hexane. The undissolved material is filtered off, triturated with another 100 ml of hexane, and discarded. The filtrate is washed with water and then saturated aqueous NaCl solution and concentrated in vacuo to an oil. This material is dissolved in ether and extracted with 2 N HCl solution. The phases are separated and the ether phase is extracted with 2 N HCl solution. The combined acid extracts are washed with ether and then extracted with dichloromethane, keeping the two extracts separated. The first extract affords an oil which crystallizes upon standing for 18 hours. This material is triturated with petroleum ether and the solid is filtered and washed with petroleum ether until nearly colorless needles are obtained, m.p. s 51°, 55°–57° C. The filtrate is concentrated in vacuo to give an oil, which is combined with the oil obtained from the second dichloromethane extract and chromatographed on silica gel, using acetone as solvent. Another portion of purified free base is obtained as an oil which crystallizes rapidly on standing. The hydrochloride salts prepared by dissolving the free base in 250 ml of ether, filtering and treating the filtrate with HCl-saturated ether solution until acidic to wet pH paper. The resulting colorless solid is filtered, washed with ether and dried to afford a colorless salt, mp s 180°, 182°–184° C. This material is recrystallized by dissolving in a boiling mixture of 200 ml of ethylacetate and 150 ml of acetone, filtering hot and boiling down the filtrate to obtain crystalline needles of trans-1-methyl-3-phenyl-4-phenylthiopiperidine hydrochloride, mp s 167°, 168°–171° C.

Analysis: Calculated for $C_{18}H_{21}NS.HCl$: 67.58%C; 6.93%H; 4.38%N; 10.03%S. Found: 67.71%C; 7.00%H; 4.22%N; 10.02%S.

EXAMPLE 41

Cis-1-methyl-3-phenyl-4-phenylthiopiperidine hydrochloride 7.72 ml of tri-n-butylphosphine are added under nitrogen to a suspension of 7.91 g of N-phenylthiophthalimide in 75 ml of benzene. After 5 minutes, 4.55 g of the free base of trans-1-methyl-3-phenyl-4-piperidinol of Example 1 are added to the resultant solution all at once. A rise in temperature to 31° C. occurs and a precipitate begins to form. After stirring the mixture for 18 hours at room temperature under nitrogen the precipitate is filtered off and washed well with hexane. The filtrate is concentrated in vacuo to an oil, which is stirred for 72 hours with 250 ml of hexane. The solid which forms is filtered off, washed well with hexane, and the filtrate is concentrated in vacuo to an oil. This material is taken up in 250 ml of ether and extracted with 2 N HCl solution. The acid extracts are backwashed with 50 ml of ether and then extracted with dichloromethane. The dichloromethane extracts are washed successively with 10% aqueous NaOH solution, water, saturated aqueous NaCl solution, dried over anhydrous $Na_2SO_4$, filtered, and concentrated in vacuo to an oil. This material is dissolved in about 200 ml of ether and treated dropwise with an HCl-saturated ether solution until the mixture is acidic to wet pH paper. After stirring for an hour the crude hydrochloride is filtered, washed with ether and air-dried to afford a colorless solid, mp s 185°, 203°–212° C. This material is dissolved in boiling acetone, filtered hot, and the filtrate boiled down to yield crystals. The recrystallized solid is filtered, washed with cold acetone, then ether and dried to afford crystals of cis-1-methyl-3-phenyl-4-phenylthiopiperidine hydrochloride, mp s 219°, 222.5°–225° C.

Analysis: Calculated for $C_{18}H_{21}NS.HCl$: 67.58%C; 6.93%H; 4.35%N; 10.03%S. Found: 67.60%C; 6.94%H; 4.34%N; 10.06%S.

EXAMPLE 42

Trans-4-(4-fluorophenylthio)-1-methyl-3-phenylpiperidine hydrochloride 12.21 ml of tri-n-butylphosphine at 15° C. are added to a suspension of 13.28 g of 4-fluorophenylthiophthalimide in 50 ml of dry benzene. After 5 minutes a slurry of 7.13 g of 1-methyl-3-phenyl-4-piperidinol (a mixture of isomers of Example 1) in 70 ml of benzene is added to the solution to form a precipitate. After stirring 18 hours at room temperature under a nitrogen atmosphere, the mixture is filtered, and the solid is washed with hexane. The filtrate is concentrated in vacuo to an oil, which is stirred for about 72 hours with 400 ml of hexane. The mixture is filtered and a resultant gummy solid is washed well with hexane. The filtrate is concentrated in vacuo to an oil, which is taken up in 400 ml of ether and extracted with 2 N HCl solution. The acid extracts are then extracted with dichloromethane. The dichloromethane extracts are washed with 10% by weight aqueous NaOH solution, then with saturated aqueous NaCl solution, dried over anhydrous $Na_2SO_4$, and concentrated in vacuo to an oil. This material is chromatographed on silica gel using acetone as solvent. A purified trans isomer and a purified cis isomer are obtained as oils. The trans isomer is dissolved in ether and treated with an HCl-saturated ether solution. The crude hydrochloride salt is filtered, washed with ether, and dried to afford a solid, m.p. s 208°, 211°–213° C. This material is suspended in 75 ml of boiling ethyl acetate. The addition thereto of 100 ml of acetone produces a solution. The mixture is boiled down to a volume of about 125 ml, at which point crystallization begins to occur. Needles of trans-4-(4-fluorophenylthio)-1-methyl-3-phenylpiperidine hydrochloride, m.p. s 209°, 211°–212.5° C., are obtained.

Analysis: Calculated for $C_{18}H_{20}FNS \cdot HCl$: 63.98%C; 6.27%H; 4.15%N; 9.49%S. Found: 63.88%C; 6.25%H; 4.05%N; 9.66%S.

EXAMPLE 43

Cis-4-(4-fluorophenylthio)-1-methyl-3-phenylpiperidine fumarate

The procedure of Example 41 is repeated except that the cis isomer is dissolved in 100 ml of ether and treated with a solution of 0.62 g of fumaric acid in a mixture of 15 ml of absolute ethanol and 35 ml of ether. Removal of the solvent in vacuo and trituration of the resulting gum with a boiling mixture of ether and ethyl acetate causes solidification to occur. A cis fumarate, mp s 159°, 161°–163° C. is thus obtained. Recrystallization from acetone affords cis-4-(4-fluorophenylthio)-1-methyl-3-phenylpiperidine fumarate, mp 162.5°–163.5° C. dec.

EXAMPLE 44 a.

Trans-4-(4-nitrophenoxy)-3-phenyl-1-phenylacetylpiperidine

A solution comprising 0.76 ml phenylacetyl chloride in 25 ml of $CHCl_3$ is added dropwise, with stirring, at room temperature and under nitrogen, to a mixture of 1.56 g of trans-4-(4-nitrophenoxy)-3-phenylpiperidine, the free base of example 4 b., 0.8 ml of triethylamine and 50 ml of $CHCl_3$ (dried over molecular sieves). The resulting reaction mixture is stirred for two hours at room temperature and is washed with water and saturated aqueous NaCl solution. The organic phase is filtered and concentrated in vacuo to a cloudy gum. This gum is chromatographed on silica gel, using $CHCl_3$ and then a methanol/$CHCl_3$ mixture. A foam of trans-4-(4-nitrophenoxy)-3-phenyl-1-phenylacetylpiperidine which can not be crystallized is obtained.

b.

Trans-4-(4-nitrophenoxy)-1-phenethyl-3-phenylpiperidine hydrochloride 7.2 ml of a 1.0 M solution of borane in THF is cooled to 2° C. and the temperature is maintained between 2° and 5° C. during addition of a solution of 1.78 g of trans-4-(4-nitrophenoxy)-3-phenyl-1-phenylacetylpiperidine in 10 ml of dry THF. Upon completion of the addition the mixture is slowly heated to reflux under nitrogen. After one hour at reflux the mixture is cooled to room temperature and 5 ml of 6 N HCl solution are added dropwise with stirring. The mixture is reheated and the THF distilled off over a two-hour period. The residue is basified with 10% aqueous NaOH solution and is extracted with ether and dichloromethane. The combined organic extracts are washed with water, then with saturated aqueous NaCl solution, dried over $Na_2SO_4$, filtered and concentrated in vacuo to afford a crude gum. This material is dissolved in dichloromethane and treated with an HCl saturated ether solution. Removal of the solvent in vacuo and trituration of the resulting gum with ether affords a solid. This material sinters at approximately 110° C., then resolidifies and melts at 236.5°–238.5° C. Trituration of this material for 20 minutes in 25 ml of boiling acetone affords a solid, m.p. s 232°, 243°–245° C. This material is suspended in 25 ml of boiling ethyl acetate. Slow addition of 15 ml of methanol affords a solution which yields upon cooling crystals, m.p. s 249°, 252.5°–253.5° C., of trans-4-(4-nitrophenoxy)-1-phenethyl-3-phenylpiperidine hydrochloride.

Analysis: Calculated for $C_{25}H_{26}N_2O_3 \cdot HCl$: 68.40%C; 6.20%H; 6.38%N; 8.08%Cl. Found: 68.14%C; 6.08%H; 6.37%N; 8.21%Cl.

EXAMPLE 45

Trans-4-(2-fluorophenoxy)-1-methyl-3-phenylpiperidine fumarate hemihydrate

A solution of 4.79 g of diethyl azodicarboxylate in 125 ml of benzene is added dropwise under a nitrogen atmosphere at 5°–10° C. over a 90 minute period to a mixture of 4.78 g of cis-1-methyl-3-phenyl-4-piperidinol, 7.21 g of triphenylphosphine, 3.08 g of 2-fluorophenol and 125 ml of dry benzene. After the addition, the mixture is stirred for 18 hours at room temperature, then filtered, and the solid waste is washed well with hexane. The filtrate is concentrated in vacuo to an oil which is stirred 18 hours with hexane. A gummy solid is filtered off, washed with hexane, and the filtrate concentrated in vacuo to an oil. This material is taken up in ether and extracted with 2 N HCl solution. The acid extracts are extracted with dichloromethane. The dichloromethane extracts are washed with 10% by weight of aqueous NaOH solution, then with saturated aqueous NaCl solution, dried over anhydrous $Na_2SO_4$, and concentrated in vacuo to afford an oil. The oil is chromatographed on silica gel, using acetone as solvent. A purified free base is obtained as an oil. This material is dissolved in 75 ml of ether and treated dropwise with a solution of 1.44 g of fumaric acid in a mixture of 25 ml of absolute ethanol and 50 ml of ether. Scratching of the resulting solution causes crystallization to occur. The solid is filtered, washed with ether, and dried to afford a colorless solid of trans-4-(2-fluorophenoxy)-1-methyl-3-phenylpiperidine furmarate hemihydrate, m.p. partially melts 149°, 161°–167° C. Recrystallization from ethyl acetate affords the product having mp s 154°, 156° C., dec.

Analysis: Calculated for $C_{18}H_{20}FNO.C_4H_4O_4.\frac{1}{2}H_2O$: 64.38%C; 6.14%H; 3.41%N; 4.63%F. Found: 64.71%C; 5.83%H; 3.23%N; 4.40%F.

EXAMPLE 46

Trans-4-(3-fluorophenoxy)-1-methyl-3-phenylpiperidine fumarate

A solution of 4.79 g of diethyl azodicarboxylate in 125 ml of benzene is added, over a 90 minute period and at 5° C. under a nitrogen atmosphere, to a mixture of 4.72 g of cis-1-methyl-3-phenyl-4-piperidinol, 7.21 g of triphenylphosphine, 3.08 g of 3-fluorophenol and 125 ml of dry benzene. After stirring 18 hours at room temperature, the solid is filtered off and washed well with hexane. The filtrate is concentrated in vacuo to an oil, which is stirred 18 hours with hexane. The resulting mixture is filtered, and the resultant gummy solid is washed well with hexane. The filtrate is concentrated in vacuo to an oil which is taken up in ether and extracted with 2 N HCl solution. The acid extracts are then extracted with dichloromethane. The dichloromethane extracts are washed with 10% by weight aqueous NaOH solution, then with saturated aqueous NaCl solution, dried over $Na_2SO_4$, and concentrated to afford an oil. This material is chromatographed on silica gel, using acetone as solvent. An oil is thus obtained, which is taken up in ether and treated dropwise with a solution of 1.55 g of fumaric acid in a mixture of 100 ml of ether and 50 ml of absolute ethanol. The solvent is removed in vacuo and the resulting gum is triturated to a solid with ether. The solid is filtered, washed with ether, and dried to afford a solid, mp s 160°, 161°–164° C. Recrystallization from ethyl acetate and then from a mixture of ethyl acetate and acetone affords trans-4-(3-fluorophenoxy)1-methyl-3-phenylpiperidine fumarate, mp s 155°, 156.5°–158° C.

Analysis: Calculated for $C_{18}H_{20}FNO.C_4H_4O_4$: 65.82%C; 6.03%H; 3.49%N; 4.73%F. Found: 65.70%C; 6.03%H; 3.43%N; 4.69%F.

EXAMPLE 47

Trans-1-ethoxycarbonyl-4-(4-fluorophenoxy)-3-phenylpiperidine

A mixture of 3.49 g of trans-4-(4-fluorophenoxy)-1-methyl-3-phenylpiperidine of Example 30, 2.53 g of anhydrous potassium carbonate, and 28 ml of dry benzene are treated all at once under a nitrogen atmosphere with 1.75 ml of ethyl chloroformate. After 1 hour at ambient temperature, the mixture is refluxed 18 hours, then cooled and partitioned between ether and water. The phases are separated and the aqueous phase is extracted with ether. The combined ether extracts are washed with 2 N HCl solution, then with saturated aqueous NaCl solution, dried over anhydrous $Na_2SO_4$, filtered and concentrated in vacuo to a gum which eventually crystallizes to a solid of trans-1-ethoxycarbonyl-4-(4-fluorophenoxy)-3-phenylpiperidine, m.p. s 78°, 80°–82.5° C.

Analysis: Calculated for $C_{20}H_{22}FNO_3$: 69.95%C; 6.46%H; 4.08%N. Found: 69.82%C; 6.45%H; 3.90%N.

EXAMPLE 48

Trans-4-(4-fluorophenoxy)-3-phenylpiperidine fumarate

A mixture of 3.44 g of trans-1-ethoxycarbonyl-4-(4-fluorophenoxy)-3-phenylpiperidine of Example 47, 50 ml of absolute ethanol and 26 ml of 20% aqueous NaOH solution is refluxed 18 hours under a nitrogen atmosphere. The ethanol is removed in vacuo, and the aqueous residue is partitioned between water and ethyl acetate. The aqueous phase is extracted with ethyl acetate, and the combined organic extracts are washed with saturated aqueous NaCl solution, dried over anhydrous $Na_2SO_4$, and concentrated in vacuo to an oil which quickly crystallizes to a solid. The solid is triturated with hexane and filtered to afford a solid, m.p. 99°–101° C. This material is dissolved in 100 ml of ether and treated dropwise with a solution of 1.05 g of fumaric acid in a mixture of 60 ml of ether and 15 ml of absolute ethanol. The resultant solid is filtered, washed with ether and dried to afford a salt of trans-4-(4-fluorophenoxy)-3-phenylpiperidine fumarate, m.p. s 142.5°, 143° C. dec.

Analysis: Calculated for $C_{17}H_{18}FNO.C_4H_4O_4$: 65.10%C; 5.73%H; 3.62%N; 4.90%F. Found: 64.87%C; 5.74%H; 3.54%N; 4.76%F.

EXAMPLE 49

Cis-4-(3-chlorophenoxy)-3-phenyl-1-(2,2,2-trichloroethoxycarbonyl)piperidine

A mixture of 2.48 g of the free base cis-4-(3-chlorophenoxy)-1-methyl-3-phenylpiperidine, of Example 36, 1.14 g of anhydrous potassium carbonate and 30 ml of dry benzene is treated with 1.42 ml of 2,2,2-trichloroethyl chloroformate. After 30 minutes at room temperature the mixture is refluxed 18 hours. Another 0.36 ml of chloroformate is added, and the mixture is refluxed another 4 hours. The mixture is then cooled and partitioned between 100 ml of ether and 50 ml of water. The aqueous phase is extracted with 50 ml of ether, and the combined organic extracts are washed with 2 N HCl solution, saturated aqueous NaCl solution, and dried over $Na_2SO_4$. Concentration in vacuo affords a mixture of a solid and an oil which is triturated with 25 ml of ether and then diluted with hexane to a volume of about 125 ml. After refrigeration for 18 hours the mixture is filtered, the solid is washed with hexane, and the filtrate is washed successively with 10% aqueous NaOH solution, water, and saturated aqueous NaCl solution. After drying over $Na_2SO_4$ the solution is concentrated in vacuo to a gum. Chromatography of this material on silica gel affords a colorless gum of cis-4-(3-chlorophenoxy)-3-phenyl-1-(2,2,2-trichloroethoxycarbonyl)piperidine.

Analysis: Calculated for $C_{20}H_{19}Cl_4NO_3$: 51.86%C; 4.13%H; 30.62%Cl; 3.02%N. Found: 51.68%C; 4.04%H; 30.28%Cl; 2.96%N.

EXAMPLE 50 a. Ethyl 3-amino-N-(2-ethoxycarbonylethyl)-2-phenylpropionate oxalate 8.14 g of ethyl atropate are added dropwise with stirring under a nitrogen atmosphere to 5.95 g of crude ethyl β-alanate. After stirring 18 hours at room temperature the mixture is taken up in ether and extracted with 2 N HCl solution. The combined acid extracts are made basic with 10% aqueous NaOH solution and extracted with ether. The combined ether extracts are dried and concentrated in vacuo to an oil (free base). This material is taken up in ether and treated with a solution of oxalic acid in ether. The resulting precipitate is filtered, washed with ether and dried to afford a solid of ethyl 3-amino-N-(2-ethoxycarbonylethyl)-2-phenylpropionate oxalate, m.p. s 165°, 166.5°–167° C. dec.

Analysis: Calculated for $C_{16}H_{23}NO_4 \cdot (CO_2H)_2$: 56.39%C; 6.57%H; 3.65%N. Found: 56.40%C; 6.48%H; 3.67%N.

b. Ethyl 3-amino-N-(2-methoxycarbonylethyl)-2-phenylpropionate 59.89 g of ethyl atropate are added dropwise with stirring under a nitrogen atmosphere to 38.55 g of methyl B-alanate. After stirring 18 hours at room temperature, the mixture is taken up in ether and extracted with 2 N HCl solution. The combined acid extracts are made basic with 10% aqueous NaOH solution and extracted with ether. The combined ether extracts are washed with aqueous NaCl solution, dried over anhydrous $Na_2SO_4$, and concentrated in vacuo to afford a crude product of ethyl 3-amino-N-(2-methoxycarbonylethyl)-2-phenylpropionate.

c. 3-Phenyl-4-piperidone hemioxalate

A solution of 72.18 g of ethyl 3-amino-N-(2-methoxycarbonylethyl)-2-phenylpropionate, of Example 50b, above, in a mixture of 10 ml of absolute ethanol and 350 ml of benzene, is added dropwise under nitrogen over a 20 minute period to a suspension of 23.62 g of sodium hydride (as a 50% dispersion) in 100 ml of anhydrous benzene. After completion of the addition, the mixture is refluxed for 45 minutes. The mixture is then cooled and treated with 250 ml of 6 N HCl solution. After removal of the benzene in vacuo, the aqueous residue is treated with another 850 ml of 6 N HCl solution, and this mixture is refluxed under nitrogen for 165 minutes. The mixture is cooled, basified with approximately 320 ml of 50% aqueous NaOH solution and extracted with dichloromethane. The combined organic extracts are washed with saturated NaCl solution, dried over anhydrous $Na_2SO_4$, and concentrated in vacuo to afford a crude solid. Trituration of this material with ether affords a pale orange crude product, mp s 92°, 94°–97° C. A portion of this material is dissolved in dichloromethane and a solution of oxalic acid in ether is added dropwise with stirring. The resulting solid is filtered off, washed with ether, and then triturated for 10 minutes in 15 ml of boiling methanol. After cooling to room temperature and allowing to stand for 1 hour a resultant colorless solid is filtered, washed with methanol and then ether to afford a product of 3-phenyl-4-piperidone hemioxalate, mp 185.5°–186° C., dec.

Analysis: Calculated for $C_{11}H_{13}NO \cdot \frac{1}{2}(CO_2H)_2$: 65.44%C; 6.41%H; 6.36%N. Found: 65.08%C; 6.30%H; 3.17%N.

d. Cis-3-phenyl-4-piperidinol

A solution of 1.75 g of the free base 3-phenyl-4-piperidone of Example 50c, above, in 10 ml of dry THF is cooled to 5° C. and trated dropwise with 15 ml of lithium tri-secondarybutylborohydride in THF over a ten minute period under nitrogen. After the addition the mixture is stirred 18 hours at room temperature, then cooled to 0°–10° C. during dropwise addition of 10 ml of 10% aqueous NaOH solution. This is followed by addition of 7 ml of 30% aqueous hydrogen peroxide solution added at a rate sufficient to keep the pot temperature between 30°–40° C. The mixture is then stirred 18 hours at room temperature, followed by 1 hour of refluxing. The mixture is cooled and the phases are separated. The aqueous phase is extracted with chloroform. The combined organic phases are concentrated in vacuo to oil which is treated with 50 ml of cyclohexane and reconcentrated to an oil. This material is taken up in chloroform, and the solution is washed with saturated aqueous NaCl solution, and dried over anhydrous $Na_2SO_4$. Concentration in vacuo affords an oil which solidifies upon trituration with ether. A solid is then obtained, mp s 111°, 114°–117° C. Recrystallization from benzene affords cis-3-phenyl-4-piperidinol, mp s 115°, 117°–119° C.

Analysis: Calculated for $C_{11}H_{15}NO$: 74.54%C; 8.53%H; 7.90%N. Found: 74.20%C; 8.51%H; 7.62%N.

EXAMPLE 51

Trans-3-phenyl-4-piperidinol

A mixture of 0.9 g of the free base, 3-phenyl-4-piperidone of Example 50c, above, 0.19 g of sodium borohydride and 15 ml of absolute ethanol is stirred at room temperature for 6 hours under a nitrogen atmosphere. The mixture is then treated with 25 ml of saturated aqueous NaCl solution and extracted with dichloromethane. The combined organic extracts are washed with saturated aqueous NaCl solution, dried over anhydrous $Na_2SO_4$ and concentrated in vacuo to a gum which TLC shows to be a mixture of cis and trans isomers, with the trans isomer predominant. Trituration of this material with benzene gives a well formed solid which is filtered off after allowing the mixture to stand 18 hours. The solid is washed with benzene and then hexane, and dried in vacuo to afford a solid, m.p. s 99°, 115°–127° C., which TLC showed contained only a small amount of the cis isomer. This material is taken up in 10 ml of boiling benzene, filtered, and boiled down to a volume of approximately 5 ml of solution to afford a solid of trans-3-phenyl-4-piperidinol, m.p. s 125.5°, 127°–128.5°, which TLC showed to be pure trans isomer.

Analysis: Calculated for $C_{11}H_{15}NO$: 74.54%C; 8.53%H; 7.90%N. Found: 75.02%C; 8.30%H; 7.68%N.

EXAMPLE 52

Trans-4-(3-methoxyphenoxy)-1-methyl-3-phenylpiperidine hydrochloride

A solution of 6.22 g of diethyl azodicarboxylate in 175 ml of benzene is added dropwise at 5°–9° C. under nitrogen over a 90 minute period to a mixture of 6.82 g of cis-1-methyl-3-phenyl-4-piperidinol, 10.31 g of triphenylphosphine, 4.88 g of m-methoxyphenol and 175 ml of dry benzene. After stirring 18 hours at room temperature the mixture is filtered and the solid is washed well with hexane. The filtrate is concentrated in vacuo to an oil. This material is stirred 18 hours with 350 ml of hexane. The liquid is filtered off, and the solid is triturated with hexane and then with 100 ml of ether. The solids are discarded and the filtrates are combined and concentrated in vacuo. The resulting oil is dissolved in 350 ml of ether and extracted with 2 N.HCl solution. The acid extracts are then extracted with dichloromethane. The combined dichloromethane extracts are washed with 10% aqueous NaOH solution, then with saturated aqueous NaCl solution, and dried over anhydrous Na$_2$SO$_4$. Concentration affords an oil. This material is chromatographed on silica gel, using acetone as solvent to yield a free base as an oil. This material is taken up in 125 ml of ether, filtered through a Celite pad, and the filtrate is treated with HCl-saturated ether until acidic to wet pH paper. The solvent is removed in vacuo. Trituration with fresh ether causes solidification to occur to yield a crude salt, mp s 165°, 169°–172° C. Recrystallization from acetone affords crystals of trans-4-(3-methoxyphenoxy)-1-methyl-3-phenylpiperidine hydrochloride, mp s 193°, 195°–196.5° C.

Analysis: Calculated for C$_{19}$H$_{23}$NO$_2$.HCl: 68.35%C; 7.25%H; 4.20%N; 10.62%Cl. Found: 68.25%C; 7.08%H; 4.09%N; 10.28%Cl.

EXAMPLE 53

Trans-4-(2-chlorophenoxy)-1-methyl-3-phenylpiperidine hydrochloride

A solution of 4.79 g of diethyl azodicarboxylate in 125 ml of anhydrous benzene is added dropwise at 4° C. under nitrogen over a 90 minute period to a mixture of 4.78 g of cis-1-methyl-3-phenyl-4-piperidinol of Example 1g, 7.21 g of triphenylphosphine, 3.54 g of 2-chlorophenol and 125 ml of anhydrous benzene. The mixture is stirred 18 hours at room temperature under nitrogen and then is filtered. The solid is washed well with hexane and the filtrate is concentrated in vacuo. The residue is triturated 18 hours with 250 ml of hexane and then filtered. The solid is washed well with hexane, triturated with ether and then filtered. The filtrates are combined and concentrated in vacuo to an oil. An ether solution of this material is made and is then extracted with 2 N HCl solution. The acid extracts are washed with ether, followed by extraction with dichloromethane. The dichloromethane extracts are washed with 10% aqueous NaOH solution, then with saturated NaCl solution, dried over anhydrous Na$_2$SO$_4$ and concentrated in vacuo to an oil. This material is chromatographed on silica gel, using acetone as a solvent to obtain an oil. This oil is dissolved in ether and treated dropwise with an HCl-saturated ether solution to yield a salt. The salt is filtered and washed with ether to afford a solid, mp s 230°, 232°–234° C. This material suspended in 25 ml of boiling ethyl acetate and acetone is gradually added to the boiling mixture until a solution is obtained. The solution is filtered hot and boiled down to start crystallization to yield a solid, mp 233°–235.5° C. of trans-4-(2-chlorophenoxy)-1-methyl-3-phenylpiperidine hydrochloride.

Analysis: Calculated for C$_{18}$H$_{20}$ClNO.HCl: 63.91%C; 6.26%H; 4.14%N. Found: 64.14%C; 6.26%H; 4.02%N.

EXAMPLE 54 a. Cis-3-(2-fluorophenyl)-1-methyl-4-piperidinol

A solution of 7.98 g of 3-(2-fluorophenyl)-1-methyl-4-piperidone in 40 ml of dry tetrahydrofuran is cooled to 5° C. under nitrogen and treated dropwise with 49 ml of a 1.0 molar tetraydrofuran solution of lithium trisecondary butylborohydride, keeping the pot temperature below 10° C. The mixture is then stirred 18 hours at room temperature under nitrogen. The mixture is cooled while 175 ml of 10% aqueous NaOH solution are added, keeping the pot temperature below 10° C. 117 ml of 30% H$_2$O$_2$ solution are added to the cooled mixture at a rate sufficient to keep the pot temperature at 30°–40° C. The mixture is stirred for 18 hours at ambient temperature followed by refluxing for one hour under nitrogen. The mixture is cooled and the phases are separated. The aqueous phase is extracted with dichloromethane and the combined organic phases are concentrated in vacuo. The residue is treated with 250 ml of cyclohexane and the mixture is concentrated. The residue is partitioned between dichloromethane and saturated NaCl solution. The dichloromethane phase is dried over anhydrous Na$_2$SO$_4$, filtered and concentrated in vacuo to a solid. This material is triturated with ether, filtered and dried to afford a solid. This material is recrystallized from benzene to afford cis-3-(2-fluorophenyl)-1-methyl-4-piperidinol, m.p. 158.5°–160° C.

Analysis: Calculated for C$_{12}$H$_{16}$FNO: 68.87%C; 7.71%H; 6.70%N. Found: 68.84%C; 7.79%H; 6.58%N.

b.

Trans-4-(4-fluorophenoxy)-3-(2-fluorophenyl)-1-methylpiperidine fumarate

The procedure of Example 53 is repeated with cis-3-(2-fluorophenyl)-1-methyl-4-piperidinol and 4-fluorophenol to yield trans-3-(2-fluorophenyl)-4-(4-fluorophenoxy)-1-methylpiperidine. This compound is treated with a solution of fumaric acid in ether containing ethanol to yield trans-4-(4-fluorophenoxy)-3-(2-fluorophenyl)-1-methylpiperidine fumarate, m.p. 205.5°–206.5° C. The crude salt is recrystallized from isopropanol to afford colorless crystals, m.p. 205.5°–206.5.

We claim:

1. A method of preparing the trans isomer form of a compound of the formula

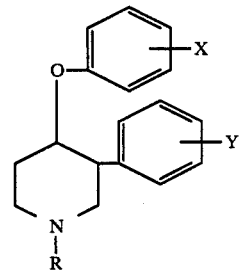

or a physiologically acceptable salt or stereoisomer thereof in which R is hydrogen, loweralkyl, cycloalkylloweralkyl, loweralkenyl, loweralkynyl, loweralkanoyl, cycloalkylloweralkanoyl, —COOR$_1$ or —R$_2$PhZ; R$_1$ is loweralkyl, loweralkenyl or —CH$_2$CCl$_3$; R$_2$ is loweralkylene, oxyloweralkylene, loweralkylenecarbonyl, carbonylloweralkylene or alkylene ethylene ketal; Ph is phenyl or phenylene; Z is hydrogen, halogen, loweralkyl, loweralkoxy, hydroxy, nitro or amino; and X and Y are the same or different and each can be hydrogen, loweralkyl, halogen, nitro, trifluoromethyl, loweralkoxy or cyano, which comprises reacting in the presence of triphenylphosphine and diethylazodicarboxylate a cis 3-phenyl-4-piperidinol of the formula

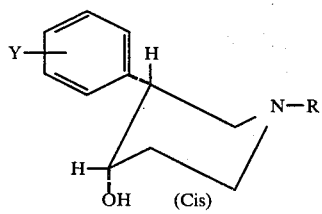

in which R and Y are as defined with a phenol of the formula

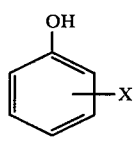

where X is as defined.

2. A method of preparing a cis isomer form of a compound of the formula

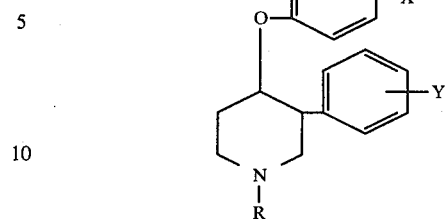

or a physiologically acceptable salt or stereoisomer thereof in which R is lower alkanoyl or —COOR₁; R₁ is loweralkyl, loweralkenyl or —CH₂CCl₃; and X and Y are the same or different and each can be hydrogen, loweralkyl, halogen, nitro, trifluoromethyl, loweralkoxy or cyano, which comprises reacting in the presence of triphenylphosphine and diethylazodicarboxylate a trans 3-phenyl-4-piperidinol of the formula

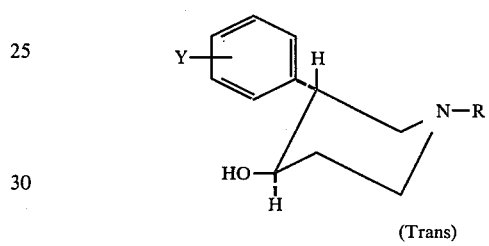

in which R and Y are as defined with a phenol of the formula

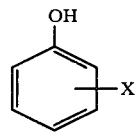

where X is as defined.

* * * * *